United States Patent [19]

Nishijima et al.

[11] Patent Number: 4,540,653

[45] Date of Patent: Sep. 10, 1985

[54] METHOD OF IMPROVING THE LIGHT RESISTANCE OF A DYE IMAGE

[75] Inventors: Toyoki Nishijima; Kaoru Onodera, both of Odawara, Japan

[73] Assignee: Konishiroku Photo Industry Co., Ltd., Tokyo, Japan

[21] Appl. No.: 643,812

[22] Filed: Aug. 23, 1984

[30] Foreign Application Priority Data

Aug. 31, 1983 [JP] Japan ................................ 58-160929

[51] Int. Cl.³ ........................... G03C 7/40; G03C 7/26
[52] U.S. Cl. .................................... 430/372; 430/386; 430/551; 430/554; 430/555; 430/558
[58] Field of Search ............... 430/372, 551, 554, 555, 430/558, 386

[56] References Cited

U.S. PATENT DOCUMENTS

| | | | |
|---|---|---|---|
| 4,245,018 | 1/1981 | Hara et al. | 430/551 |
| 4,326,022 | 4/1982 | Ito et al. | 430/551 |
| 4,346,165 | 8/1982 | Sawada et al. | 430/551 |
| 4,369,243 | 1/1983 | Credner et al. | 430/223 |
| 4,407,940 | 10/1983 | Nakamura et al. | 430/551 |

Primary Examiner—J. Travis Brown
Attorney, Agent, or Firm—Frishauf, Holtz, Goodman & Woodward

[57] ABSTRACT

A photographic element comprising a support having thereon a layer containing a dye that is formed by the reaction of an anilino-type magenta coupler with the oxidized product of a color developing agent, the said layer comprising an organic solvent having a dielectric constant of not more than 6.5 and at least one of metallic complexes having the following Formula [I], Formula [II] or Formula [III]:

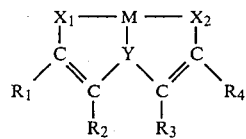

Formula [I]

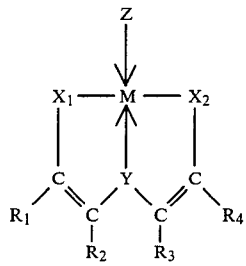

Formula [II]

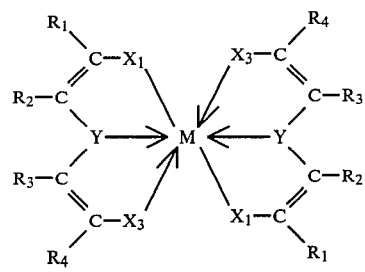

Formula [III]

In Formulas [I], [II] and [III], M is a nickel atom, copper atom, cobalt atom, palladium atom or platinum atom; $X_1$ and $X_2$ each is an oxygen atom, sulfur atom or $-NR_5-$ (wherein $R_5$ is a hydrogen atom, an alkyl, aryl or hydroxyl radical); $X_3$ is a hydroxyl or mercapto radical; Y is an oxygen atom or sulfur atom; $R_1$, $R_2$, $R_3$ and $R_4$ each is a hydrogen atom or a halogen atom or a cyano radical, or an alkyl, aryl, cycloalkyl or heterocyclic radical which each is bonded directly or through a divalent combining radical to a carbon atom; and at least one of the $R_1-R_2$ and $R_3-R_4$ combinations is allowed to form a 5- or 6-member cyclic ring together with the carbon atoms which are bonded with each other; and Z is a compound coordinateable to M.

24 Claims, No Drawings

METHOD OF IMPROVING THE LIGHT RESISTANCE OF A DYE IMAGE

BACKGROUND OF THE INVENTION

1. Field of the Invention

The present invention relates to a method for rendering a dye image resistant to light, and more particularly to a method for improving the light resistance of a dye image that is formed on a silver halide color photographic light-sensitive material.

2. Description of the Prior Art

As the generally applicable method for forming a dye image by use of a silver halide color photographic light-sensitive material there is known, as described in James et al, "The Theory of Photographic Process," 4th ed., 1977, a method for forming dyes by the reaction of photographic couplers with the oxidized product of a color developing agent, which method uses magenta, yellow and cyan couplers as the photographic couplers for ordinary color reproductions, and an aromatic primary amine-type color developing agent as the color developing agent, and in which the magenta and yellow couplers react with the oxidized product of the aromatic primary amine-type developing agent to form dyes such as azomethine dyes, and the cyan coupler reacts with the same oxidized product of the color developing agent to form a dye such as an indoaniline dye.

One of basically desired natures for the dye image formed by the reaction of the oxidized product of the color developing agent with the magenta, yellow and cyan photographic couplers is that these dyes be not discolored with age even when exposed over a long period to light or stored under high-temperature and highly moist conditions. Above all, since the resistance to light of a dye image formed from the magenta coupler has been unsatisfactory, adequate improvement in this aspect has long been awaited.

There have until now been many proposals for improving the light resistance of a dye image formed from a magenta coupler, which proposals include, for example, the use of a selected less-discolorable magenta coupler, the protection of a magenta dye image from ultraviolet rays by use of an ultraviolet-absorbing agent, the use of an antidiscoloration agent to prevent a magenta dye image from its discoloration by light, and incorporating a light resistance-providing radical into a magenta coupler.

Of these the method which uses an ultraviolet-absorbing agent requires a relatively large amount of an ultraviolet-absorbing agent in order to give a satisfactory light resistance to a resulting dye image. This method, however, has the disadvantage that the color of the ultraviolet-absorbing agent itself stains the magenta dye image area or margin area of a photographic sheet; or because the use of the ultraviolet-absorbing agent alone is not enough to prevent possible discoloration of the dye image due to visible rays the improvement of the magenta dye image in its resistance to light naturally has its limits.

As the method which uses an antidiscoloration agent there is known a method which uses an antidiscoloration agent having a phenolic hydroxyl radical or a radical that is hydrolyzed to produce a phenolic hydroxyl radical. As such the antidiscoloration agent, those compounds have been proposed which include, e.g., phenols and bisphenols; pyrogallol and gallic acid and esters thereof; α-tocopherols and acyl derivatives thereof; hydroquinone derivatives; 6-hydroxychromans; 5-hydroxychroman derivatives; 6,6'-hydroxy-2,2'-bis-spirochromans, and the like. These, however, are not considered to be capable of sufficiently preventing a magenta dye image from its possible discoloration.

Further, as another method for improving the light resistance of a magenta dye image, British Pat. No. 1,451,000 describes improvement of the stability of an organic light-absorbing compound by use of an azomethine light-cut compound having its maximum absorption wavelength on a longer wavelength side than the maximum wavelength of the above organic light-absorbing compound. In this method, however, the azomethine light-cut compound itself has a color, which varies the tone of the organic light-absorbing compound, so that it cannot be practically used for improving the light resistance of a dye image.

Japanese Patent Publication Open to Public Inspection (hereinafter referred to as Japanese Patent O.P.I. Publication) Nos. 67649/1975, 62826/1979, 62987/1979, 65185/1979, 69580/1979, 72780/1979, 82234/1979, 82385/1979 and 136581/1974 describe methods of improving the light resistance of a dye image by using metallic complexes. However, these particular metallic complexes described in these publications themselves have conspicuous colors which would adversely affect the color tone, color purity, whiteness of the white area, etc., of a resulting dye image, so that particularly in such a photographic element for direct appreciation use which attaches importance to aesthetics as, e.g., a dye image-bearing color photographic paper, etc., the use of such color degrading metallic complexes may bring about large defective troubles. These known metallic complexes, when added to the silver halide emulsion layer(s) constituting a silver halide color photographic light-sensitive material, tend to accelerate the deterioration of the characteristics (occurrence of desensitization, fog, etc.) of the silver halide emulsion. Further, these metallic complexes are disadvantageous in respect that they cannot be added in as much a quantity as required to obtain a sufficient antidiscoloration effect because they are generally less soluble in organic solvents.

Further, those metallic complexes as described in Japanese Patent O.P.I. Publication Nos. 99340/1981 and 168625/1981, although their adverse effect upon the characteristics of a silver halide emulsion is comparatively small, have their own color which still remain unsolved, so that they have the large disadvantage that they, when used in a photographic element for direct appreciation use, impair the beautifulness of a dye image. And certain metallic complexes, if used in a silver halide emulsion and when the emulsion is stored over an extensive period, deteriorate the light-resistant effect of and cause yellow stain on the emulsion.

As has been described above, these image dye's light resistance improving methods using the ultraviolet-absorbing agent, antidiscoloration agent or azomethine light-cut compound, although light-resistant effects can be expected to a certain extent from them, have the problem that the ultraviolet-absorbing agent's or azomethine light-cut compound's own color produces stain on resulting dye images. The method using metallic complexes, although an adequate light-resistant effect can be expected, is disadvantageous in respect of many such problems that the complex causes stain on resulting images due to its own color; deteriorates the photographic characteristics; is less soluble in solvents; and so forth. And some metallic complexes increase stain and deteriorate the light resistance-improving effect during a long-period storage. Accordingly, every metallic complex has some disadvantage, so that any metallic complex is not considered suitable for practical application. Thereupon, the realization of a method capable of attaining adequate light resistance of dye images by use of a novel metallic complex has been desired, the metallic complex being free from such the disadvantages as color stain, deterioration of photographic characteristics, less solubility, and increase in discoloration as well as in color stain during a long-period storage.

SUMMARY OF THE INVENTION

It is, therefore, a first object of the present invention to provide a method of improving the light resistance of a dye image capable of preventing the dye image from possible discoloration by light by way of improving the stability to light of the dye formed as a result of the reaction of photographic couplers, particularly a magenta coupler, with the oxidized product of a color developing agent.

It is a second object of the present invention to provide a method for improving the light resistance of a dye image, which causes no deterioration of the light resistance nor increase in color stain during a long-period storage.

It is a third object of the present invention to provide a method for improving the light resistance of a dye image, which is capable of preventing the dye image from possible discoloration by light without deteriorating the hue of the dye and the whiteness of a white area of the image.

It is a fourth object of the present invention to provide a method of improving the light resistance of a dye image, which is capable of preventing the dye image from possible discoloration without adversely affecting the photographic characteristics.

It is a fifth object of the present invention to provide a method for improving the light resistance of a dye image, which is capable of preventing the dye image from possible discoloration by use of a metallic complex having a high solubility in organic solvents.

The above objects of the present invention are accomplished by a method for improving the light resistance of a dye image, which uses a photographic element comprising a support having thereon a layer containing a dye that is formed by the reaction of an anilino-type magenta coupler with the oxidized product of a color developing agent, the said layer comprising an organic solvent having a dielectric constant of not more than 6.5 and at least one of metallic complexes having the following Formula [I], Formula [II] or Formula [III]:

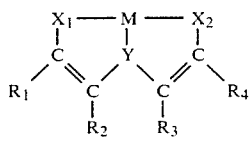

Formula [I]

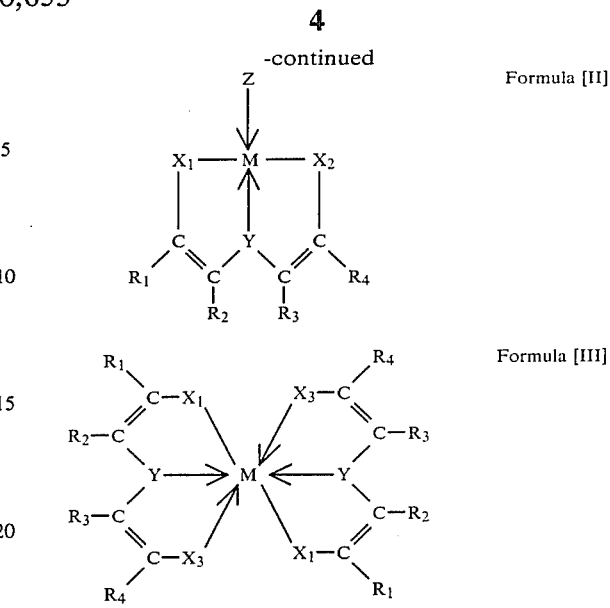

in Formulas [I], [II] and [III], M is a nickel atom, copper atom, cobalt atom, palladium atom or platinum atom; $X_1$ and $X_2$ each is an oxygen atom, sulfur atom or $-NR_5-$ (wherein $R_5$ is a hydrogen atom, an alkyl, aryl or hydroxyl radical); $X_3$ is a hydroxyl or mercapto radical; Y is an oxygen atom or sulfur atom; $R_1$, $R_2$, $R_3$ and $R_4$ each is a hydrogen atom or a halogen atom or a cyano radical, or an alkyl, aryl, cycloalkyl or heterocyclic radical which each is bonded directly or through a divalent combining radical to a carbon atom; and at least one of the $R_1-R_2$ and $R_3-R_4$ combinations is allowed to form a 5- or 6-member cyclic ring together with the carbon atoms which are bonded with each other; and Z is a compound coordinatable to M.

According to the method of improving the light resistance of a dye image of the present invention, the stability to light of a dye image can be improved and the discoloration by light of the dye image can be sufficiently prevented without deteriorating the whiteness of the white area as well as the hue of the dye image on a processed photograph formed by the reaction of the photographic coupler with the oxidized product of the color developing agent of the present invention and without causing such deteriorated photographic characteristics as desensitization, fog, and the like.

The application of the organic solvent of the present invention to the metallic complex of the invention prevents the deterioration of the light resistance of a dye image caused during or after a long-period storage. Further, a large disadvantage, the yellow stain caused during a long-period storage, can be solved concurrently.

These effects were all beyond expectation.

Further, the metallic complex of the present invention, because of its high solubility in organic solvents, can be added in a sufficient quantity to a silver halide photographic light-sensitive material, so that it is capable of increasing the light resistance of a dye image satisfactorily without bringing about any trouble such as deposition of the complex. Thus, the dye image's light resistance-improving effect can be displayed remarkably by the dye formed from the combination of the metallic complex of the invention with the coupler of the invention, and further, particularly, from the combination of the dye having Formula [XI] with the organic solvent of the invention. Further, the combined use of the antidiscoloration agent of the invention enables to obtain an excellent light resistance-improving effect.

DETAILED DESCRIPTION OF THE INVENTION

The present invention will be illustrated further in detail.

In the present invention, those metallic complexes having Formula [I], [II] or [III] (these are hereinafter called generically "the metallic complex of the invention") may be used alone or in combination of not less than two of them. In either of the single or combined use the metallic complexes, the objects of the present invention can be accomplished sufficiently.

The $X_1$ and $X_2$ of Formulas [I] and [II] are allowed to be either the same as or different from each other, and each represents oxygen, sulfur or $-NR_5-$ [wherein $R_5$ is hydrogen or an alkyl radical (such as methyl, ethyl, n-propyl, i-propyl, n-butyl, t-butyl, i-butyl, benzyl, etc.), an aryl radical (such as, e.g., phenyl, tolyl, naphthyl, etc.) or a hydroxyl radical], and preferably oxygen or a sulfur atom, and more preferably oxygen.

The $X_3$ of Formula [III] (the two $X_3$s are allowed to be either the same as or different from each other) is a hydroxyl or mercapto radical, and preferably a hydroxyl radical.

The Y of each of Formulas [I], [II] and [III] (the two Ys of Formula [III] are allowed to be either the same as or different from each other) represents oxygen or sulfur, and preferably sulfur.

The $R_1$, $R_2$, $R_3$ and $R_4$ in each of Formulas [I], [II] and [III] are allowed to be the same as or different from one another, and each represents hydrogen, a halogen (fluorine, chlorine, bromine or iodine), a cyano radical, or an alkyl radical (such as methyl, ethyl, propyl, butyl, hexyl, octyl, dodecyl, hexadecy, etc., the alkyl radicals each being allowed to be either a straight-chain alkyl radical or a branched-chain alkyl radical), an aryl radical (such as phenyl, naphthyl), a cycloalkyl radical (such as cyclopentyl, cyclohexyl), or a heterocyclic radical (such as pyridyl, imidazolyl, furyl, thienyl, pyrrolyl, pyrolidinyl, quinolyl, morpholinyl, etc.), the said alkyl, aryl or heterocyclic radical being bonded to a carbon atom directly or through a divalent combining radical [such as $-O-$, $-S-$, $-NH-$, $-NR_5'-$ {wherein $R_5'$ is a monovalent radical such as a hydroxyl radical or an alkyl radical (such as methyl, ethyl, n-propyl, i-propyl, n-butyl, t-butyl, i-butyl, etc.), or aryl radical (such as phenyl, tolyl, naphthyl, etc.)}, or $-OCO-$, $-CO-$, $-NHCO-$, $-CONH-$, $-COO-$, $-SO_2NH-$, $-NHSO_2-$, $-SO_2-$, or the like].

Of these radicals, the radical formed by the alkyl, aryl, cycloalkyl or heterocyclic alkyl radical (one of which is bonded to a carbon atom through a divalent combining radical) together with the divalent radical includes, for example, alkoxy radicals (straight-chain or branched-chain alkoxy radicals such as methoxy, ethoxy, n-butyloxy, octyloxy, etc.), alkoxycarbonyl radicals (straight-chain or branched-chain alkyloxycarbonyl radicals such as methoxycarbonyl, ethoxycarbonyl, n-hexadecyloxycarbonyl, etc.), alkylcarbonyl radicals (straight-chain or branched-chain alkylcarbonyl radicals such as acetyl, valeryl, stearyl, etc.), arylcarbonyl radicals (such as benzoyl), alkylamino radicals (straight-chain or branched-chain alkylamino radicals such as N-n-butylamino, N,N-di-n-butylamino, N,N-di-n-octylamino, etc.), alkylcarbamoyl radicals (straight-chain or branched-chain alkylcarbamoyl radicals such as n-butylcarbamoyl, n-dodecylcarbamoyl, etc.), alkylsulfamoyl radicals (straight-chain or branched-chain alkylsulfamoyl radicals such as n-butylsulfamoyl, n-dodecylsulfamoyl, etc.), alkylcarbonylamino radicals (straight-chain or branched-chain alkylacylamino radicals such as acetylamino, palmitoylamino, etc.), aryloxy radicals (such as phenoxy, naphthoxy, etc.), aryloxycarbonyl radicals (such as phenoxycarbonyl, naphthoxycarbonyl, etc.), arylamino radicals (such as N-phenylamino, N-phenyl-N-methylamino, etc.), arylcarbamoyl radicals (such as phenylcarbamoyl, etc.), arylsulfamoyl radicals (such as phenylsulfamoyl, etc.), arylcarbonylamino radicals (such as benzoylamino, etc.), and the like.

Regarding the $R_1$, $R_2$, $R_3$ and $R_4$ of each of Formulas [I], [II] and [III], the members of at least one of the $R_1$–$R_2$ and $R_1$–$R_2$ combinations are allowed to form a 5- or 6-member cyclic ring with the carbon atoms which are bonded with each other. The 5- or 6-member cyclic ring formed by the members of the at least one of the $R_1$–$R_2$ and $R_3$–$R_4$ combinations along with the carbon atoms includes at-least-one-unsaturated-bonding-having hydrocarbon rings such as, for example, cyclopentene ring, cyclohexene ring, benzene ring (including condensed benzene rings such as naphthalene ring, anthracene ring), etc., and heterocyclic rings (such as nitrogen-containing 5- or 6-member heterocyclic rings), etc.

These 5- or 6-member rings may have a substituent. The substituent includes halogens (fluorine, chlorine, bromine, iodine), cyano radical, alkyl radicals (straight-chain or branched-chain alkyl radicals having from 1 to 20 carbon atoms, such as methyl, ethyl, n-propyl, n-butyl, n-octyl, t-octyl, n-hexadecyl, etc.), aryl radicals (such as phenyl, naphthyl, etc.), alkoxy radicals (straight-chain or branched-chain alkyloxy radicals such as methoxy, n-butoxy, t-butoxy, etc.), aryloxy radicals (such as phenoxy), alkoxycarbonyl radicals (straight-chain or branched-chain alkyloxycarbonyl radicals such as n-pentyloxycarbonyl, t-pentyloxycarbonyl, n-octyloxycarbonyl, t-octyloxycarbonyl, etc.), aryloxycarbonyl radicals (such as phenoxycarbonyl), acyl radicals (straight-chain or branched-chain alkylcarbonyl radicals such as acetyl, stearoyl, etc.), acylamino radicals (straight-chain or branched-chain alkylcarbonylamino radicals such as acetamido; arylcarbonylamino radicals such as benzoylamino), arylamino radicals (such as N-phenylamino), alkylamino radicals (straight-chain or branched-chain alkylamino radicals such as N-n-butylamino, N,N-diethylamino, etc.), carbamoyl radicals (straight-chain or branched-chain alkylcarbamoyl radicals such as n-butylcarbamoyl, etc.), sulfamoyl radicals (straight-chain or branched-chain alkylsulfamoyl radicals such as N,N-di-n-butylsulfamoyl, N-n-dodecylsulfamoyl, etc.), sulfonamido radicals (straight-chain or branched-chain alkylsulfonylamino radicals such as methylsulfonylamino, etc.; arylsulfonylamino radicals such as phenylsulfonylamino, etc.), sulfonyl radicals (straight-chain or branched-chain alkylsulfonyl radicals such as mesyl, etc.; arylsulfonyl radicals such as tosyl, etc.), cycloalkyl radicals (such as cyclohexyl, etc.), and the like.

In Formulas [I], [II] and [III], the preferred form composed of the $R_1$, $R_2$, $R_3$ and $R_4$ each representing an alkyl or aryl radical is one selected from the group consisting of the 5-member ring and the 6-member ring which each is formed in such a way that at least one of the $R_1$-$R_2$ and $R_3$-$R_4$ combinations is combined with the carbon atoms that are bonded with each other, and more preferably it is of 6-member rings wherein both $R_1$-$R_2$ and $R_3$-$R_4$ combinations each is combined with the bonded carbon atoms thereof, and most preferably the rings are benzene rings.

The M of Formulas [I], [II] and [III] is preferably nickel, copper or cobalt, and more preferably nickel.

The compound coordinatable to the M, represented by the Z of Formula [II] is preferably a straight-chain or branched-chain alkyl-containing alkylamine, and more preferably an alkylamine whose alkyl's total number of carbon atoms is from 2 to 36, and more preferably from 3 to 24, the alkylamine including monoalkylamines such as, e.g., butylamine, octylamine (e.g., t-octylamine), dodecylamine (e.g., n-dodecylamine), hexadecylamine, octanolamine, etc.; dialkylamines such as, e.g., diethylamine, dibutylamine, dioctylamine, didodecylamine, diethanolamine, dibutanolamine, etc.; and trialkylamines such as, e.g., triethylamine, tributylamine, trioctylamine, triethanolamine, tributanolamine, trioctanolamine, 1,4-diaza-bicyclo[2,2,2]octane, etc.

The more preferred metallic complexes of the present invention having Formulas [I], [II] and [III] are those having the following Formulas [Ia], [IIa] and [IIIa]:

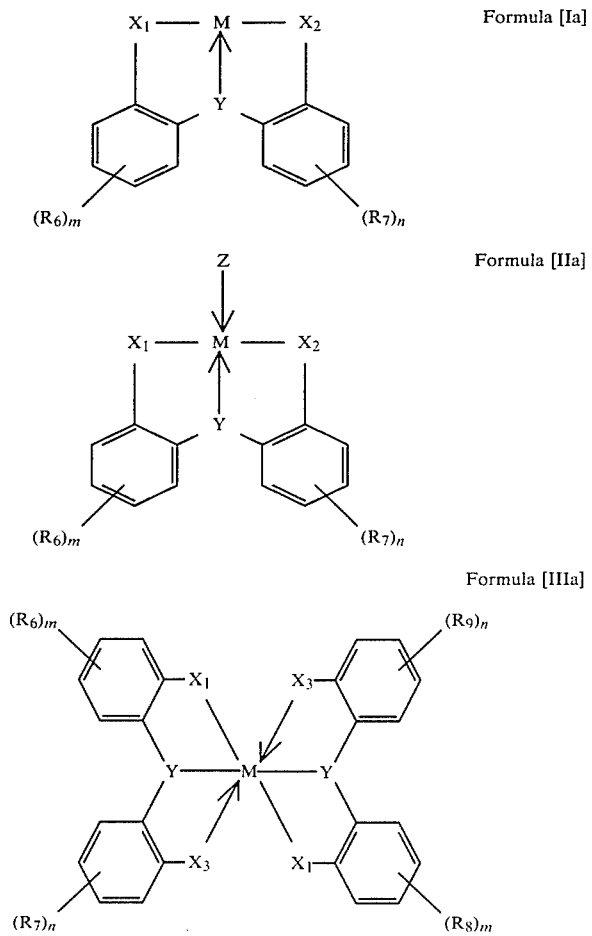

Formula [Ia]

Formula [IIa]

Formula [IIIa]

In Formulas [Ia], [IIa] and [IIIa], M, $X_1$, $X_2$, $X_3$, Y and Z are as defined and exemplified previously.

In Formulas [Ia], [IIa] and [IIIa], $R_6$, $R_7$, $R_8$ and $R_9$ each is an alkyl radical (a straight-chain or branched-chain alkyl radical having from 1 to 20 carbon atoms, such as methyl, ethyl, n-propyl, n-butyl, n-octyl, t-octyl, n-hexadecyl, etc.), an aryl radical (such as phenyl, naphthyl), an alkoxy radical (a straight-chain or branched-chain alkyloxy radical such as methoxy, n-butoxy, t-butoxy, etc.), an aryloxy radical (such as phenoxy), an alkoxycarbonyl radical (a straight-chain or branched-chain alkyloxycarbonyl radical such as n-pentyloxycarbonyl, t-pentyloxycarbonyl, n-octyloxycarbonyl, t-octyloxycarbonyl, etc.), an aryloxycarbonyl radical (such as phenoxycarbonyl), an acyl radical (a straight-chain or branched-chain alkylcarbonyl radical such as acetyl, stearoyl, etc.), an acylamino radical (a straight-chain or branched-chain alkylamino radical such as acetamido, etc.; an arylcarbonylamino radical such as benzoylamino, etc.), an arylamino radical (such as N-phenylamino), an alkylamino radical (a straight-chain or branched-chain alkylamino radical such as N-n-butylamino, N,N-diethylamino, etc.), a carbamoyl radical (a straight-chain or branched-chain alkylcarbamoyl radical such as n-butylcarbamoyl, etc.), a sulfamoyl radical (a straight-chain or branched-chain alkylsulfamoyl radical such as N,N-di-n-butylsulfamoyl, N-n-dodecylsulfamoyl, etc.), a sulfonamido radical (a straight-chain or branched-chain alkylsulfonylamino radical such as methylsulfonylamino, etc.; an arylsulfonylamino radical such as phenylsulfonylamino, etc.), a sulfonyl radical (a straight-chain or branched-chain alkylsulfonyl radical such as mesyl; an arylsulfonyl radical such as tosyl, etc.), or a cycloalkyl radical (such as cyclohexyl); and m and n each is an integer of from zero to 4.

The further preferred metallic complexes of the present invention represented by Formulas [I], [II] and [III] are those having the following Formulas [Ib], [IIb] and [IIIb]:

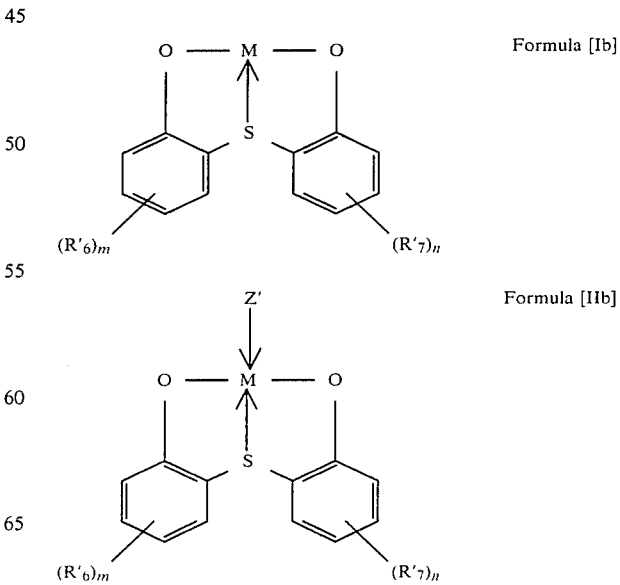

Formula [Ib]

Formula [IIb]

-continued

Formula [IIIb]

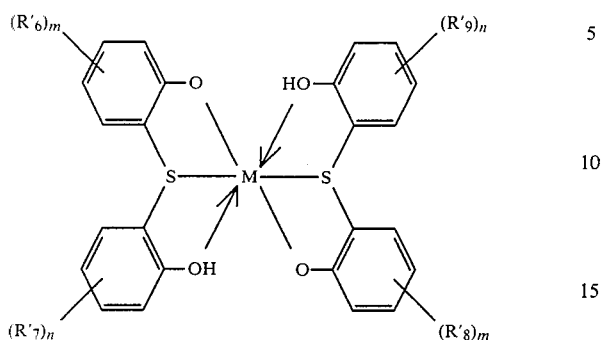

In Formulas [Ib], [II] and [IIIb], M, m and n are as defined previously; Z' is an alkylamine which includes the previously mentioned monoalkylamines, dialkylamines and trialkylamines; and $R_6'$, $R_7'$, $R_8'$ and $R_9'$ each is a straight-chain or branched-chain alkyl radical having not less than 4 carbon atoms, and preferably from 8 to 22 carbon atoms (such as n-butyl, n-octyl, t-octyl, n-hexadecyl, etc.).

The particularly preferred among those having Formulas [Ib], [IIb] and [IIIb] are those compounds having Formula [IIb].

The following are typical examples of the metallic complex of the present invention (hereinafter called the exemplified complex(es)), but the present invention is not limited thereto.

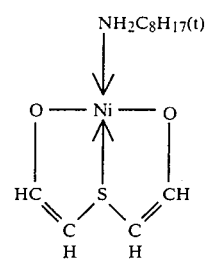  (1)

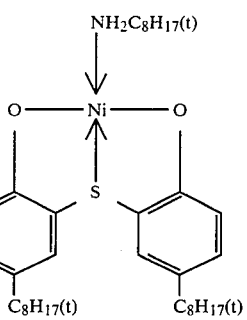  (2)

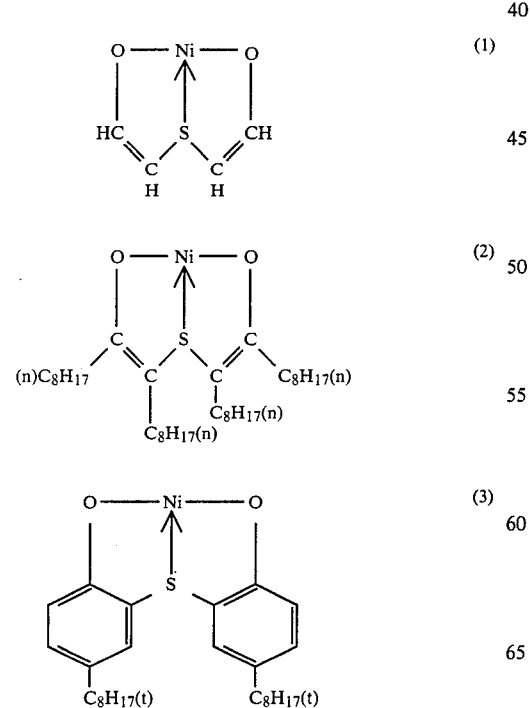

(3)

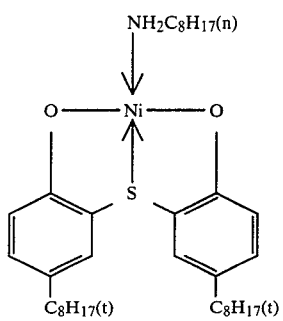  (4)

(5)

(6)

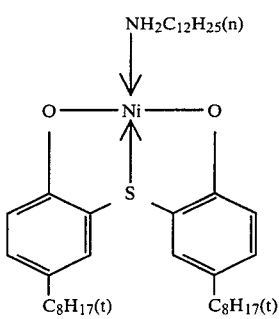  (7)

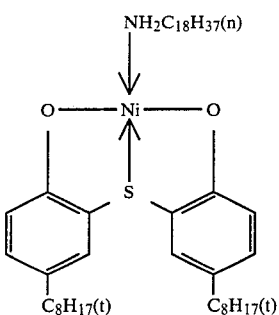  (8)

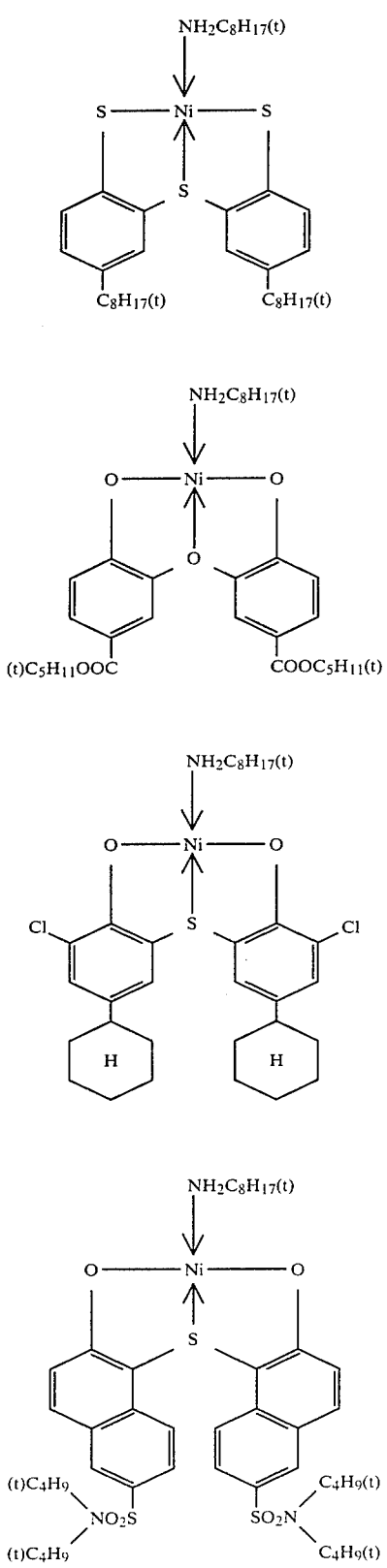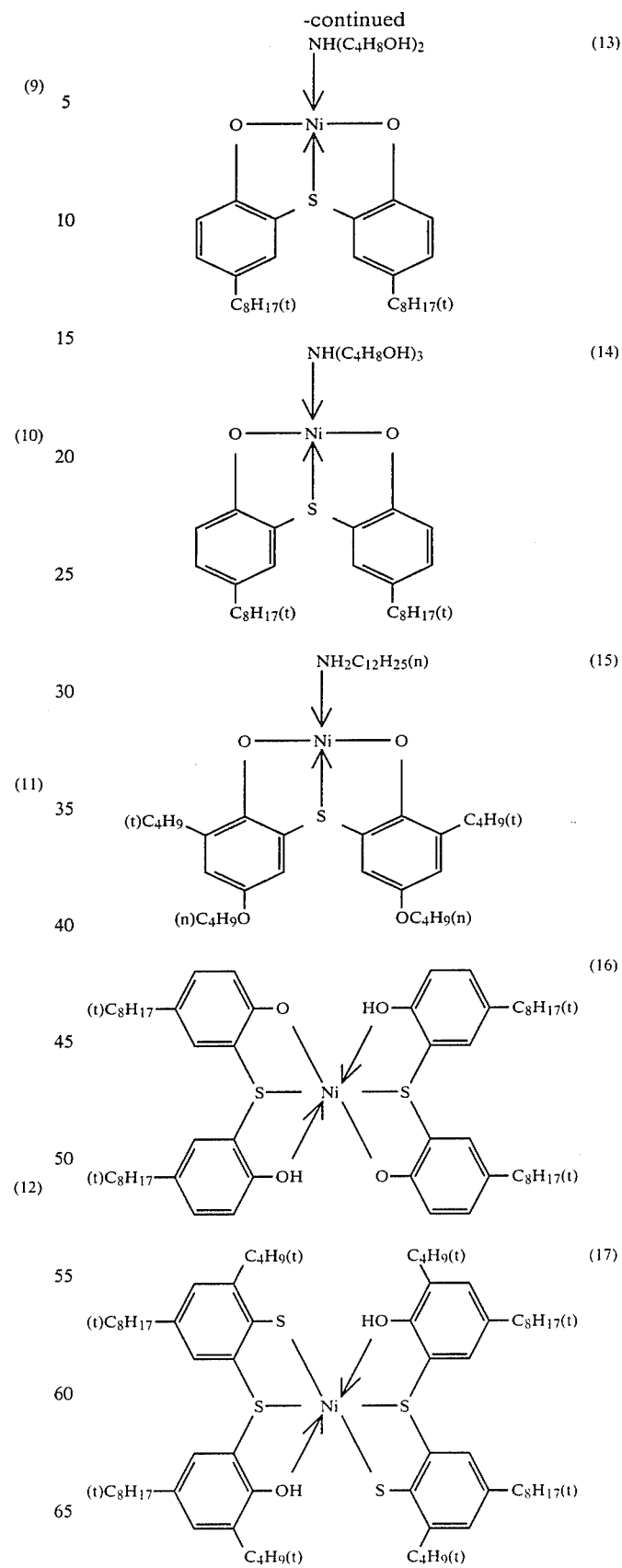

-continued

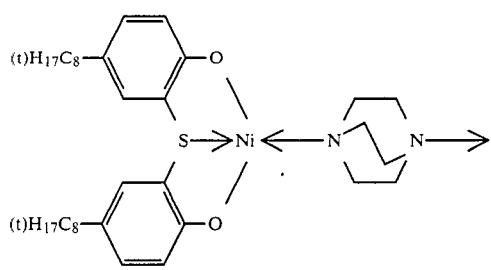 (18)

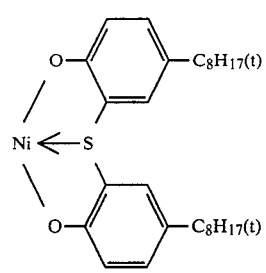

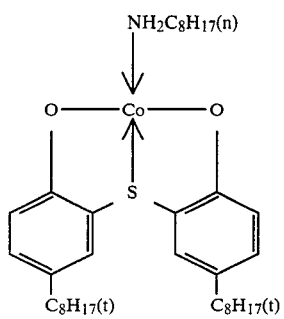 (19)

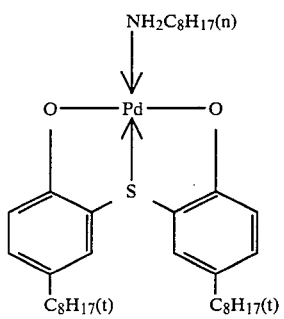 (20)

(21)

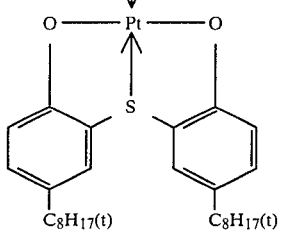 (22)

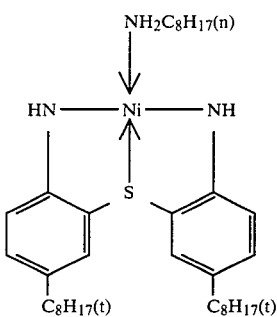 (23)

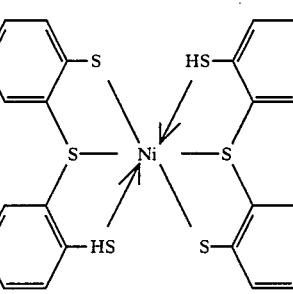 (24)

These complexes can be synthesized in the manner as described in British Pat. No. 858,890, West German OLS Pat. No. 2,042,652, and the like.

Followings are synthesis example.

SYNTHESIS EXAMPLE

Synthesis Example 1 (Preparation of Nickel Complex 16)

Toluene of 80 ml containing 12 g of 2,2'-thiobis(4-t-octylphenol) prepared in the process described in British Pat. No. 858,890 were added to 120 ml of toluene containing [2,2'-thiobis(4-t-octyl phenolate)]-aquonickel (II) exemplified in Example 1 of W. German DOS Pat. No. 2,042,652, while the mixture was being stirred under a refluxing condition. The mixture was then refluxed with heating for 4 hours. The resulted solution was concentrated at a reduced pressure by evaporating the used solvents. The residual liquid was recrystallized with toluene/petroleum ether.

Resultingly, 20 g of light-green powders which were readily soluble in ethyl acetate were obtained.

Synthesis Example 2 (Preparation of Nickel Complex 18)

Diazabicyclo[2,2,2]octane of 15 g were added to a suspension comprising 120 ml of toluene containing 17 g of [2,2'-thio-bis-(4-t-octylphenolate)]-aquonickel (II) chelate, and the mixture was refluxed with heating for 3 hours. The resulted transparent liquid was concentrated at a reduced pressure by evaporating the used solvents.

Resultingly, 12 g of light-green crystals which were readily soluble in ethyl acetate were obtained.

Synthesis Example 3 (Preparation of Nickel Complex 6)

2,2'-thiobis-4-octylphenol of 88 g were added to 500 ml of toluene, and 60 g of 2-ethyl hexylamine were further added thereto with being stirred. The resulted liquid was dropped in a solution prepared by dissolving 58 g of nickel sulfate in 200 ml of water, and a reflux with heating was made for 2 hours. A concentrated solution by which an organic layer can be separated and a solvent can be concentrated at a reduced pressure was dropped with being stirred in 600 ml of acetone, and crystallization was allowed to take place by cooling the mixture. The crystals were separated.

Resultingly, 110 g of light-green powders were obtained.

The complex of the present invention is used in a proportion of 5-100% by weight, and preferably 10-50% by weight to a quantity of the coupler of the invention. The complex of the invention and the coupler of the invention are desirable to be present together in the same oil droplets.

Any organic solvents, if they are of a dielectric constant of not more than 6.5, can be used in the present invention. Such solvents include, for example, esters such as phthalates, phosphates; organic acid amides; ketones; hydrocarbon compounds; and the like, which all are of a dielectric constant of not more than 6.5 for example, dioctylphthalate, dinonylphthalate, decarine, methylcyclohexane. The preferred are those high-boiling organic solvents having a dielectric constant of from 1.9 to 6.5 and a vapor pressure at 100° C. of not more than 0.5 mmHg. The more preferred high-boiling solvents are phthalates and phosphates. The usable solvent may be a mixture of two or more of the above compounds. In this instance it may be a mixture of any solvents as long as the mixture is of a dielectric constant of not more than 6.5. In addition, the "dielectric constant" herein means a dielectric constant at 30° C.

The phthalates which are advantageously usable in the present invention are those having the formula:

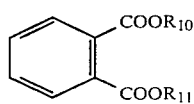

Formula [IV]

wherein $R_{10}$ and $R_{11}$ each is an alkyl radical, alkenyl radical (hexadecylethylenyl) or aryl radical (phenyl, naphtyl), provided that the total number of the carbon atoms of radicals represented by the $R_{10}$ and $R_{11}$ is from 8 to 32, and preferably from 16 to 24.

In the invention, the alkyl radical represented by the $R_{10}$ or $R_{11}$ of Formula [IV] is of straight chain or branched chain and includes, e.g., butyl, pentyl, hexyl, heptyl, octyl, nonyl, decyl, undecyl, dodecyl, tridecyl, tetradecyl, pentadecyl, hexadecyl, heptadecyl, octadecyl, and the like. The aryl radical represented by the $R_{10}$ or $R_{11}$ includes phenyl, naphtyl, and the like. The alkenyl radical includes hexenyl, heptenyl, octadecenyl, and the like.

These alkyl, alkenyl and aryl radicals each is allowed to have a single substituent or a plurality of substituents. The substituent for the alkyl and alkenyl radicals includes, e.g., halogens, alkoxy, aryl, aryloxy, alkenyl, alkoxycarbonyl radicals, and the like. The substituent for the aryl radicals includes, e.g., halogens, alkyl, alkoxy, aryl, aryloxy, alkenyl, alkoxycarbonyl radicals, and the like. Two or more of these substituents are allowed to be introduced to the foregoing alkyl, alkenyl or aryl radical.

The phosphates which are advantageously usable in the present invention are those having the formula:

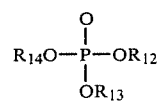

Formula [V]

wherein $R_{12}$, $R_{13}$ and $R_{14}$ each is an alkyl, alkenyl or aryl radical, provided that the total number of the carbon atoms of radicals represented by the $R_{12}$, $R_{13}$ and $R_{14}$ is from 24 to 54.

The alkyl radical represented by the $R_{12}$, $R_{13}$ or $R_{14}$ of Formula [V] includes, e.g., octyl, nonyl, decyl, undecyl, dodecyl, tridecyl, tetradecyl, pentadecyl, hexadecyl, heptadecyl, octadecyl, nonadecyl, and the like.

These alkyl, alkenyl and aryl radicals are allowed to have a single substituent or a plurality of substituents. The $R_{12}$ and $R_{13}$ is preferably an alkyl radical such as 2-ethylhexyl, n-octyl, 3,5,5-trimethylhexyl, n-nonyl, n-decyl, sec-decyl, sec-dodecyl, t-octyl, and the like.

The following are examples of the organic solvent usable in the present invention, but the invention is not limited thereto.

Exemplified Organic Solvents

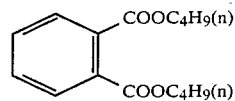
(H-1)

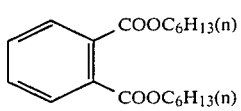
(H-2)

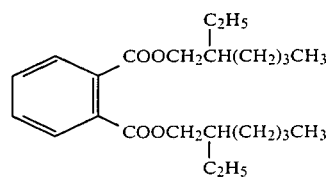
(H-3)

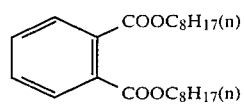
(H-4)

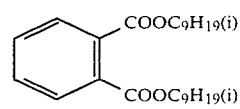
(H-5)

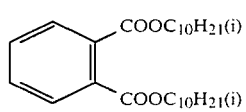
(H-6)

-continued
Exemplified Organic Solvents

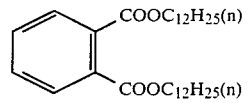 (H-7)

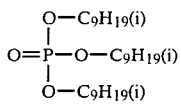 (H-8)

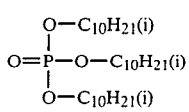 (H-9)

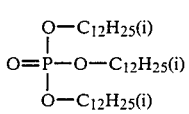 (H-10)

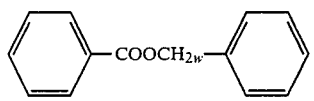 (H-11)

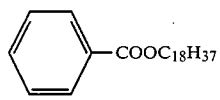 (H-12)

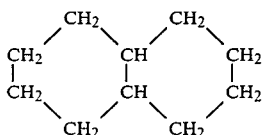 (H-13)

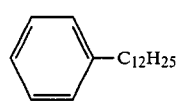 (H-14)

These organic solvents may be used in a proportion of from 25 to 150% by weight, and preferably from 50 to 100% by weight to a quantity of the anilino-type magenta coupler of the present invention.

For the combination of the complex and the organic solvent of the present invention, there may be applied any combination of a complex having Formula [I], [II] or [III] with an organic solvent of a dielectric constant of not more than 6.5, preferably the combination of a complex having [Ib], [IIb] or [IIIb] with an organic solvent having [IV] or [V], and more preferably the combination of a complex having [IIb] with an organic solvent having Formula [IV] or [V].

The foregoing photographic element can be one that is obtained in the manner that, for example, a silver halide color photographic light-sensitive material for ordinary color reproduction use is exposed imagewise and then processed in a color developer solution. The photographic element comprises a layer containing a dye that is formed by the reaction of a photographic coupler with the oxidized product of a color developing agent; namely a layer containing an unformed dye or a layer bearing a completed dye image. The silver halide photographic light-sensitive material used to obtain such a photographic element can be, e.g., a color negative or positive film or color photographic printing paper. Particularly when it is used as the color photographic paper to be used for direct appreciation, the effect of the present invention can be displayed satisfactorily.

Those photographic silver halide light-sensitive materials, including the color photographic printing paper, applicable to the present invention may be for monochromatic use or for multicolor use. The silver halide photographic light-sensitive material for multicolor use, for the subtractive color reproduction, is of a construction comprising normally photographic magenta, yellow and cyan couplers-containing silver halide emulsion layers and non-light-sensitive layers which are superposedly coated in a given order on a support. Where the photographic light-sensitive material is a color photographic printing paper, it comprises a support having thereon, for example, an yellow coupler-containing blue-sensitive silver halide emulsion layer, a magenta coupler-containing green-sensitive silver halide emulsion layer and a cyan coupler-containing red-sensitive silver halide emulsion layer coated in the described order from the support side. Further, arbitrary interlayers, a filter layer, and a protective layer are provided between the silver halide emulsion layers, between the support and the blue-sensitive silver halide emulsion layer, and in the position further than the red-sensitive silver halide emulsion layer from the support, respectively.

The metallic complex of the present invention may be incorporated in advance into a photographic coupler-containing, e.g., silver halide emulsion layer to thereby render the complex of the invention present together with a dye that is formed thereinside. Alternatively, the ligand part alone of the metallic complex excluding the metallic atom therefrom may be incorporated in advance into a photographic coupler-containing, e.g., silver halide emulsion layer, and then the silver halide photographic light-sensitive material is processed in, e.g., a color developer solution containing metallic ions to thereby render the produced metallic complex of the invention present together with a dye that is formed in the photographic couplercontaining layer.

Since the metallic complex of the present invention does not adversely affect the photographic characteristics of a photographic light-sensitive material, it is desirable to incorporate the complex in advance into a layer containing a photographic coupler that will form a dye thereinside.

The metallic complex of the present invention, when used in combination with an anilino-type magenta coupler (hereinafter sometimes referred to as the photographic coupler of the invention), exhibits a satisfactory light resistance-improving effect. It is, therefore, desirable to render the metallic complex of the invention present in a layer of a photographic element containing a dye that is formed by the reaction of the anilino-type magenta coupler with the oxidized product of a color developing agent, the photographic element being obtained in the manner that the metallic complex of the invention or the ligand part thereof is incorporated into an anilino-type magenta coupler-containing silver halide emulsion layer, usually a green-sensitive silver halide emulsion layer, and this silver halide photographic light-sensitive material is exposed and then processed in a color developer bath containing a color developing agent. Further both coupler and metallic complex are desirable to be present in the same oil droplets.

The foregoing anilino-type magenta coupler is preferably a 3-anilino-5-pyrazolone-type magenta coupler, and more preferably those 3-amino-5-pyrazolone-type magenta couplers having the formula:

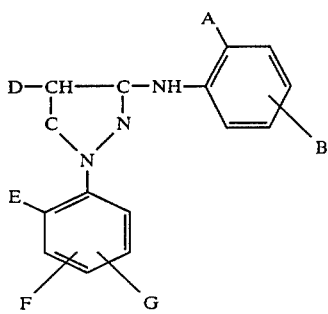

Formula [VI]

wherein A is a halogen (fluorine, chlorine, bromine or iodine), an alkyl radical (a straight-chain or branched-chain alkyl radical having from 1 to 4 carbon atoms, such as methyl, ethyl, n-propyl, t-butyl, n-butyl, etc.), an aryl radical (such as phenyl, naphthyl, etc.), an alkoxy radical (a straight-chain or branched-chain alkyloxy radical having from 1 to 4 carbon atoms, such as methoxy, ethoxy, etc.), an aryloxy radical (such as phenoxy, naphthyloxy, etc.), a hydroxyl radical, an acylamino radical (a straight-chain or branched-chain alkylacylamino radical such as ethylcarbonylamino; an arylcarbonylamino radical such as phenylcarbonylamino, etc.), cyano radical, nitro radical, or a hydrogen atom.

In Formula [VI], is hydrogen, a halogen (fluorine, chlorine, bromine or iodine) or a monovalent organic radical such as a carbonyl radical (a straight-chain or branched chain alkylcarbamoyl radical such as N-n-dodecylcarbamoyl, etc.; an arylcarbamoyl radical such as phenylcarbamoyl; an N-alkyl-N-arylcarbamoyl radical such as N-n-octyl-N-phenylcarbamoyl, etc.), an acylamino radical (a straight-chain or branched-chain alkylcarbonylamino radical such as n-tridecylcarbonylamino; an arylcarbonylamino radical such as benzoylamino, etc.), sulfamoyl radical (a straight-chain or branched-chain alkylsulfamoyl radical such as i-octylsulfamoyl, etc.; an arylsulfamoyl radical such as phenylsulfamoyl, etc.), a succinic acid imido radical, an oxycarbonyl radical (a straight-chain or branched-chain alkyloxycarbonyl radical such as methoxycarbonyl, ethoxycarbonyl, etc,; an aryloxycarbonyl radical such as phenoxycarbonyl, etc.), a sulfonamido radical (a straight-chain or branched-chain alkylsulfonamido radical such as methanesulfonamido, ethanesulfonamido, etc.; an arylsulfonamido radical such as benzenesulfonamido, etc.), an alkylamino radical (a straight-chain or branched-chain alkylamino radical such as N-n-butylamino, N,N-di-n-butylamino, etc.), succinic acid imido radical (a straight-chain or branched-chain alkylsuccinic acid imido radical such as 3-n-dodecyl-succinic acid imido, 3-octadecyl-succinic acid imido, etc.; a straight-chain or branched-chain alkylthio-succinic acid imido radical such as 3-n-dodecylthio-succinic acid imido, 3-n-octadecylthio-succinic acid imido, etc.), or the like.

In Formula [VI], D is hydrogen or a radical that can split off from the magenta coupler having Formula [VI] (e.g., an alkylthio radical such as benzylthio; an arylthio radical such as phenylthio; an alkyloxy radical such as benzyloxy; an aryloxy radical such as phenoxy; an alkylsulfo radical; a phthalic acid imido radical, or the like).

In Formula [VI], E is a halogen (fluorine, chlorine, bromine or iodine), an alkyl radical (a straight-chain or branched-chain alkyl radical such as methyl, ethyl, i-propyl, t-butyl, etc.), an alkoxy radical (a straight-chain or branched-chain alkyloxy radical such as methoxy, ethoxy, t-butoxy, etc.), an alkoxycarbonyl radical (a straight-chain or branched-chain alkyloxycarbonyl radical such as methoxycarbonyl, ethoxycarbonyl, etc.), a nitro radical, an aryloxy radical (such as phenoxy), a cyano radical or an acylamino radical (e.g., an alkylcarbonylamino radical such as methylcarbonylamino; an arylcarbonylamino radical such as benzoylamino, etc.).

In Formula [VI], F and G are the same as or different from each other, and each is hydrogen or a radical which is as defined in the above E.

The photographic coupler of the present invention, aside from those represented by Formula [VI], can be a coupler that is formed in the manner that two coupler residues which each is constituted by the D-excluded portion of Formula [VI] (the two coupler residues may be the same as or different from each other) are combined with each other through an alkylene radical such as, e.g., methylene; the so-called bis-type coupler.

Further, the photographic coupler of the present invention, aside from the above, can be a four-equivalent-type or two-equivalent-type coupler, or a polymer coupler, as described in, e.g., U.S. Pat. Nos. 3,277,155 and 3,458,315.

Typical examples of the photographic coupler of the present invention are given below, but the invention is not limited thereto.

Exemplified Couplers

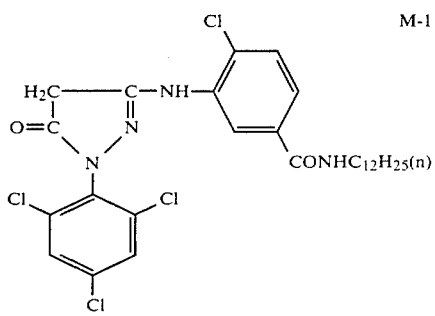

M-1

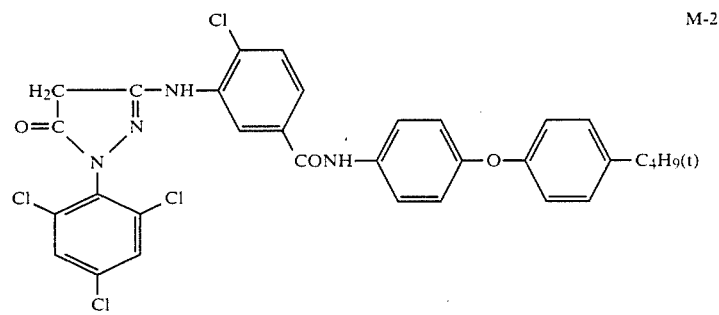

M-2

-continued
Exemplified Couplers
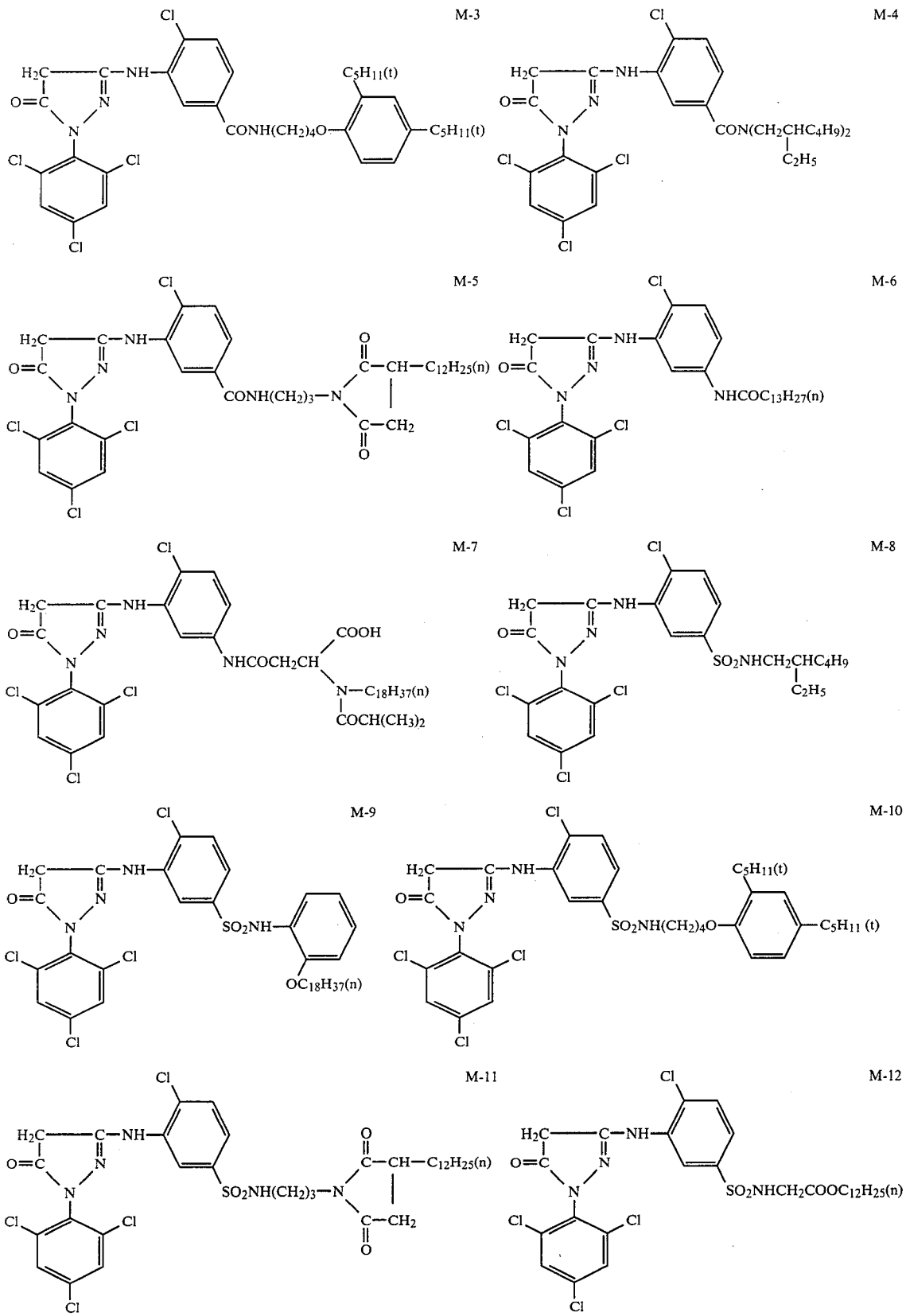

-continued
Exemplified Couplers
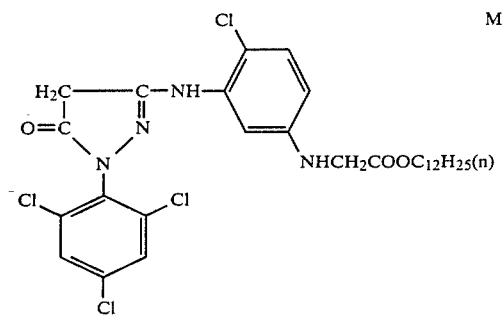
M-13
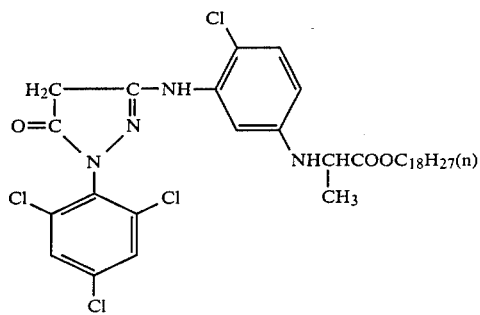
M-14
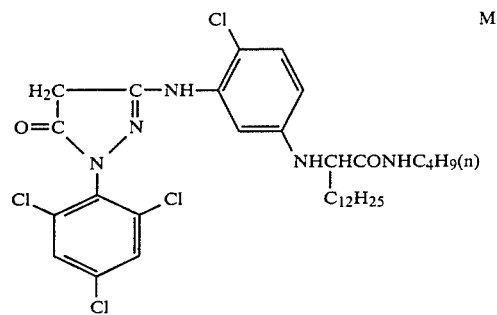
M-15
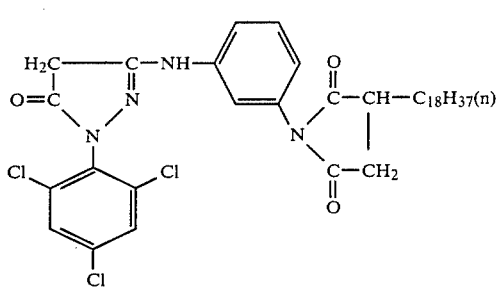
M-16
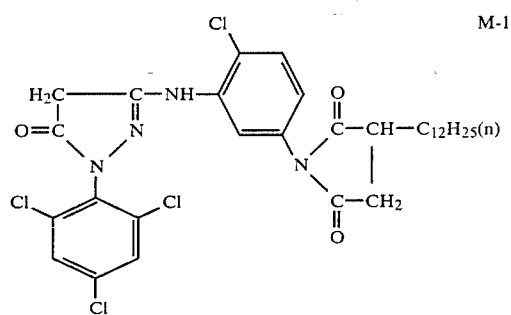
M-17
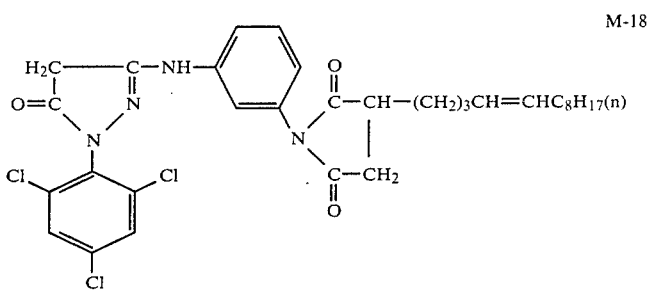
M-18
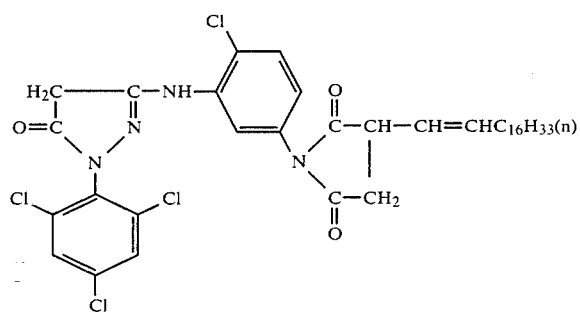
M-19
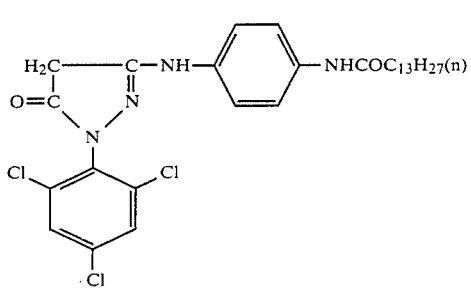
M-20
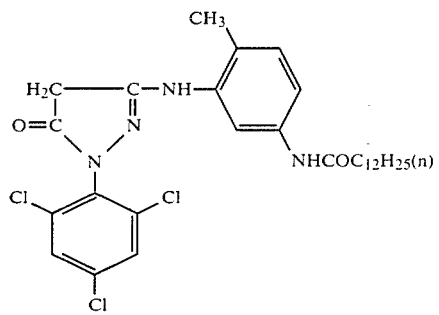
M-21
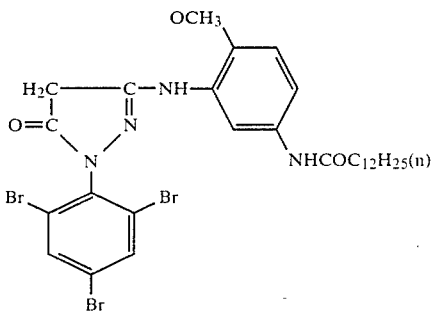
M-22

-continued
Exemplified Couplers
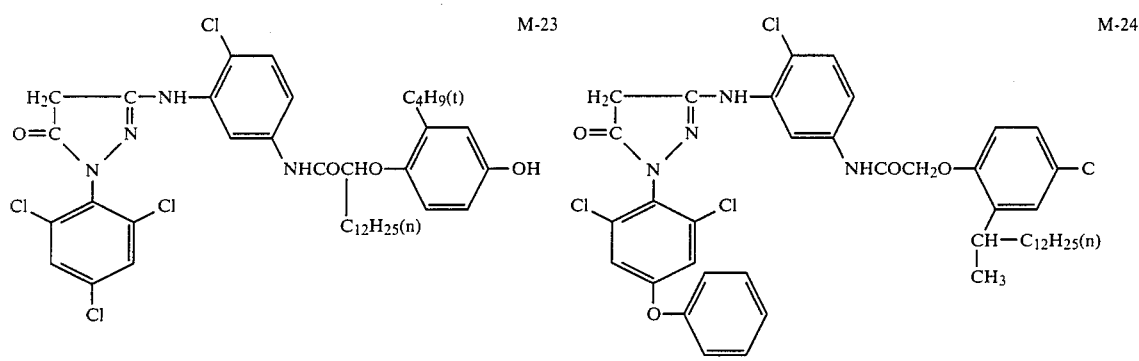
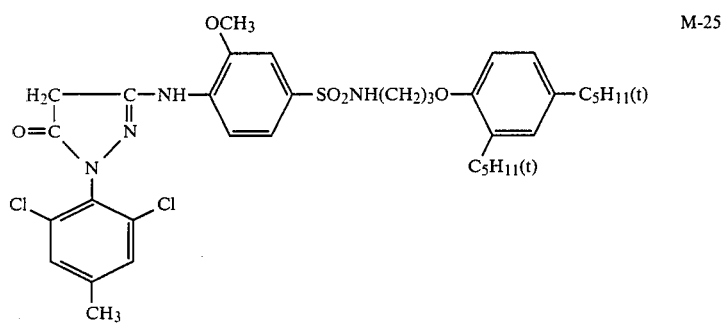
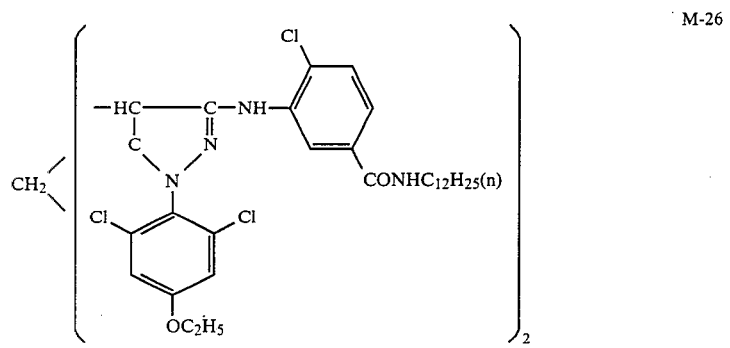
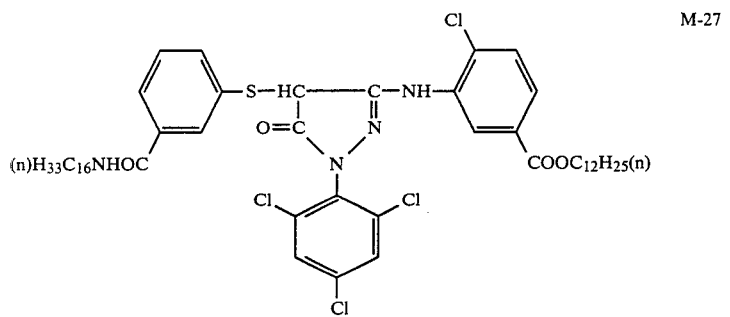

-continued
Exemplified Couplers

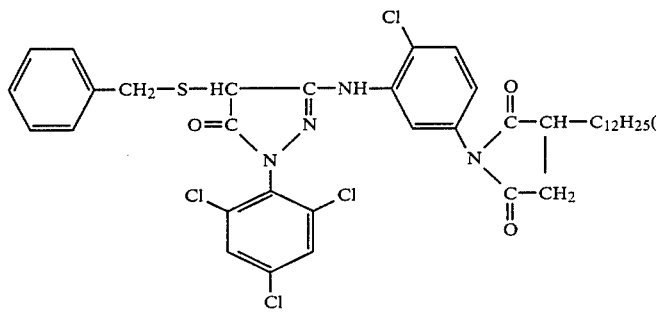

M-28

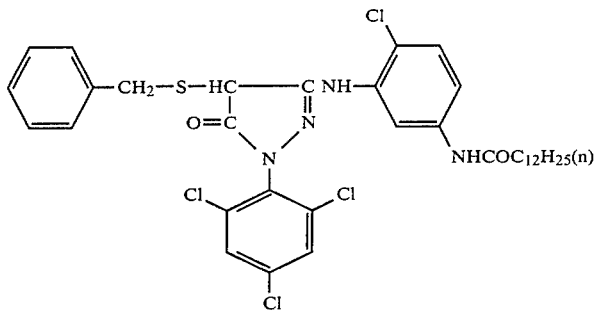

M-29

These magenta couplers can be synthesized in accordance with those methods as described in, e.g., U.S. Pat. Nos. 3,684,514 and 1,183,515; Japanese Patent Examined Publication Nos. 6031/1965, 6035/1965, 15754/1969, 40757/1970 and 19032/1971; Japanese Patent O.P.I. Publication Nos. 13041/1975, 129035/1978, 37646/1976 and 62454/1980.

These magenta couplers are coated in an amount of normally from 0.2 to 0.5 g/m².

In order to incorporate a metallic complex of the present invention or the ligand part thereof along with a photographic coupler of the invention into a silver halide emulsion layer that constitutes the silver halide photographic light-sensitive material used in the present invention, the oil-in-water-type dispersion method is suitable used. Where the oil-in-water-type dispersion method is applied, a metallic complex of the invention or the ligand part thereof and a photographic coupler of the invention are dissolved into an organic solvent of the invention, and this solution is added to an aqueous gelatin solution containing a surface active agent, and then emulsifiedly dispersed by means of a homogenizer or the like. This dispersed liquid is incorporated into a silver halide emulsion, and the emulsion is then coated on a support.

When incorporating the metallic complex of the invention or the ligand part thereof along with the photographic coupler of the invention into the silver halide emulsion layer that constitutes the silver halide emulsion, if an antidiscoloration agent having the following Formula [VII] or [VIII] is used, a remarkably improved light-resistance effect can be obtained.

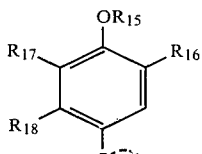

Formula [VII]

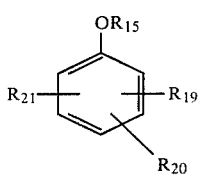

Formula [VIII]

In Formulas [VII] and [VIII], $R_{15}$ is hydrogen, an alkyl, acyl, sulfonyl, carbamoyl, sulfamoyl, alkoxyl carbonyl or trialkylsilyl radical; J is a group of nonmetallic atoms necessary to form a 5- or 6-member cyclic ring along with the bonded carbon atoms and an oxygen atom, the 5- or 6-member cyclic ring being allowed to have a bis-spiro linkage; $R_{16}$, $R_{17}$ and $R_{18}$ each is hydrogen, an alkyl, alkoxy, aryl, aryloxy, alkenyl, alkenoxy, acylamino, halogen, alkylthio, arylthio, diacylamino, alkoxycarbonyl, acyloxy, acyl or sulfonamido radical, the radicals represented by the $R_{16}$, $R_{17}$ and $R_{18}$ being allowed to be the same as or different from one another; and $R_{19}$, $R_{20}$ and $R_{21}$ each is hydrogen, hydroxy, an alkyl, alkenyl, alkoxy, aryl, aryloxy, acyloxy or alkoxycarbonyl radical, provided the total number of the carbon atoms of $R_{19}$, $R_{20}$ and $R_{21}$ is not less than 8, the radicals represented by the $R_{19}$, $R_{20}$ and $R_{21}$ being allowed to be the same as or different from one another.

Those antidiscoloration agents having Formula [VII] include spiro-bis compounds. The particularly useful spiro-bis compounds have the following Formula [VII']

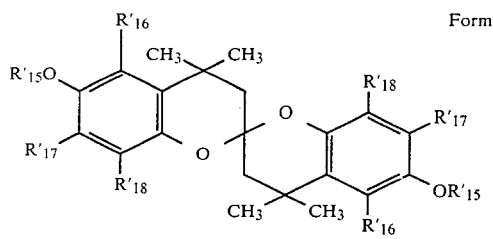

Formula [VII']

wherein $R_{15}'$, $R_{16}'$, $R_{17}'$ and $R_{18}'$ are the same as the $R_{15}$, $R_{16}$, $R_{17}$ and $R_{18}$, respectively, defined in Formula [VII].

The following are typical examples of those antidiscoloration agents represented by Formulas [VII], [VII'] and [VIII] (hereinafter referred to as the antidiscoloration agent of the invention), but the invention is not limited thereto.

Exemplified Antidiscoloration Agents (1) 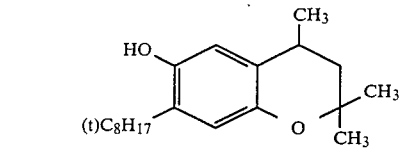

(2) 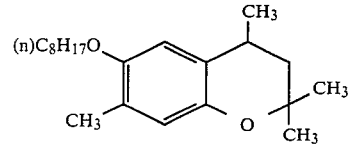

(3) 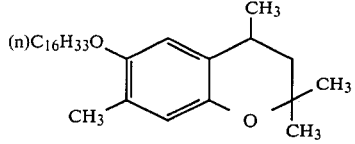

(4) 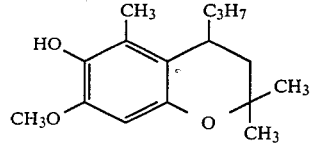

(5) 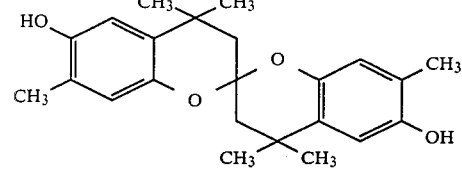

(6) 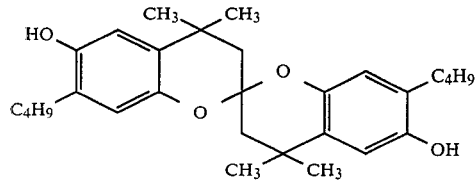

-continued
Exemplified Antidiscoloration Agents (7) 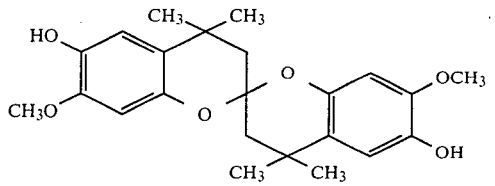

(8) 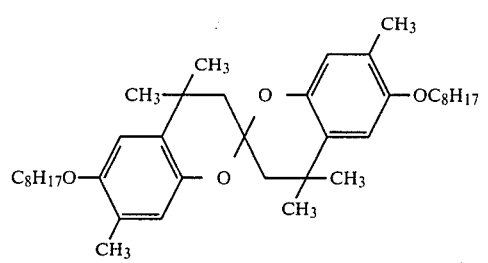

(9) 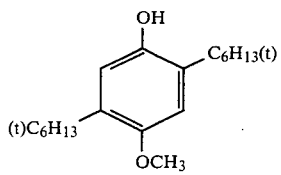

(10) 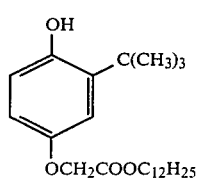

(11) 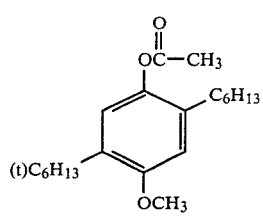

(12) 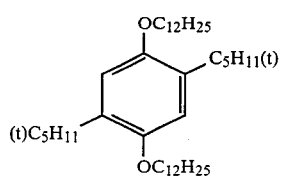

(13) 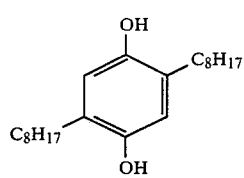

(14) 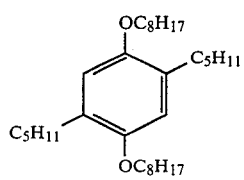

-continued
Exemplified Antidiscoloration Agents

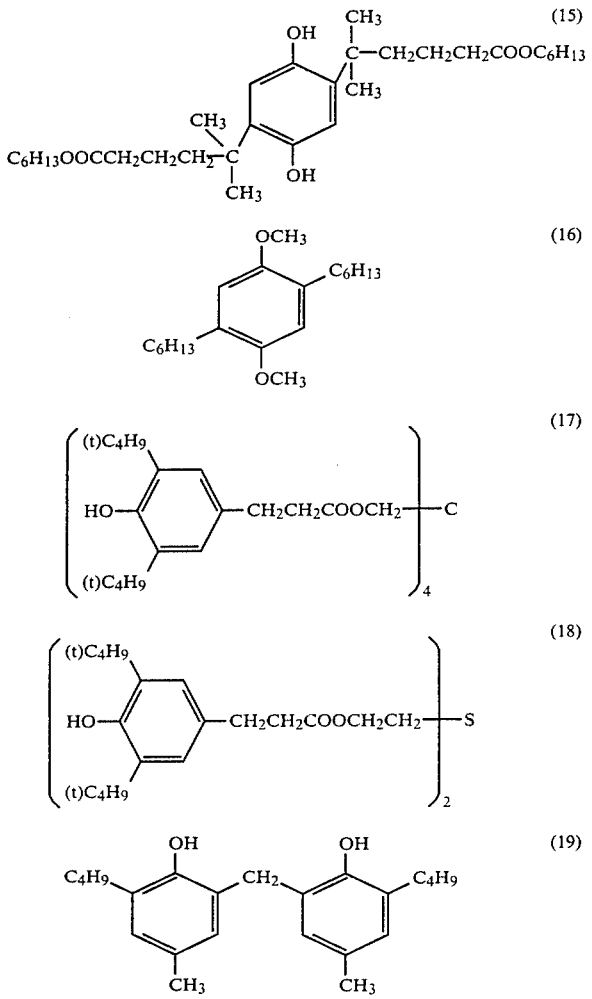

In incorporating the antidiscoloration agent of the present invention along with the metallic complex of the invention and the photographic coupler of the invention into a silver halide emulsion layer that constitutes the silver halide photographic light-sensitive material used in the invention, it is desirable to incorporate the antidiscoloration agent in a proportion of from 0.01 to 1.0 mole, and preferably from 0.1 to 0.4 mole per mole of the photographic coupler of the invention.

The silver halide used in silver halide emulsion layers that constitute the silver halide photographic light-sensitive material used in the present invention includes those silver halides arbitrarily applied to ordinary silver halide photographic emulsions, such as silver chloride, silver bromide, silver iodide, silver chlorobromide, silver iodobromide, silver chloroiodobromide, and the like. Particles of these silver halides may be either coarse-grained or fine-grained, and the distribution of the particle sizes may be either wider or narrower.

These silver halide particles may be of either a regular crystal or a twin crystal, whose surface is composed of (100) and (111) faces in any arbitrary proportion. The crystal structure of these silver halide particles may be either homogeneous from the inside through outside or heterogeneous between the outside and the inside. Further, these silver halides may be of the type of forming a latent image chiefly on the surface thereof of the type of forming a latent image inside the particles thereof.

These silver halide particles may be prepared in any manner known to those skilled in the art.

The silver halide photographic light-sensitive material used in the present invention may contain development accelerator, hardener, surfactant, antistain agent, lubricant, and other useful additives, in addition to the previously mentioned various additives.

The support applicable to the silver halide photographic light-sensitive material used in the present invention includes known support materials such as plastic-laminated paper, baryta paper, synthetic paper, polyethylene terephthalate film, triacetate film, and the like. These supports, in order to increase their adherence to the silver halide emulsion layer, are usually subjected to various treatments.

The foregoing color developing agent of the present invention includes aromatic primary amine-type color developing agents such as, e.g., o-aminophenols, p-aminophenols, p-phenylenediamines, and the like. The preferred among these aromatic primary amine color developing agents are those having the following Formulas [IX] and [X]:

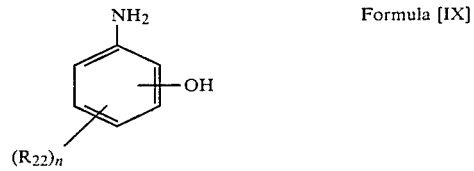

Formula [IX]

wherein the hydroxyl radical is combined in the ortho or para position with respect to the amino radical; $R_{22}$ is an alkyl (preferably an alkyl radical having from 1 to 4 carbon atoms), the alkyl being allowed to have a substituent which includes alkylsulfonamido, alkoxycarbonyl, hydroxyl, and the like; and n is an integer of from zero to 4,

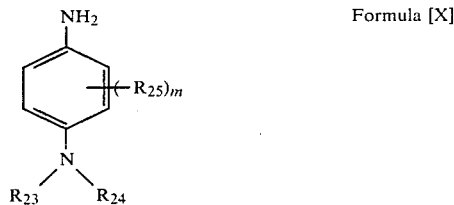

Formula [X]

wherein $R_{23}$ and $R_{24}$ each is hydrogen or an alkyl radical (preferably an alkyl radical having from 1 to 4 carbon atoms), provided both $R_{23}$ and $R_{24}$ do not represent hydrogen concurrently, the said alkyl represented by each of $R_{23}$ and $R_{24}$ being allowed to have a substituent which includes alkylsulfonamido, alkoxycarbonyl, hydroxyl, and the like, the $R_{23}$ and $R_{24}$ being allowed to form a cyclic radical (e.g., morpholino, piperidino, etc.) with the bonded nitrogen atom; $R_{25}$ is a halogen or an alkyl radical (preferably an alkyl radical having from 1 to 4 carbon atoms); and m is an integer of from zero to 4.

The particularly preferred among aromatic primary amine-type color developing agents represented by Formula [X] are those having the following Formula [X']:

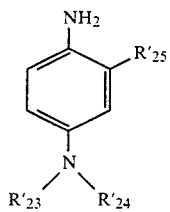

Formula [X']

wherein $R_{23}'$ and $R_{24}'$ each is an alkyl radical having from 1 to 4 carbon atoms, the alkyl radical being allowed to have a substituent which includes alkylsulfonamido, alkoxycarbonyl, hydroxyl, and the like; and $R_{25}'$ is an alkyl radical having from 1 to 4 carbon atoms.

The aromatic primary amine-type color developing agent represented by Formula [IX], [X] or [X'] may also be used in the form of an acid salt such as hydrochloride or sulfate, or of an organic acid salt such as p-toluenesulfonate, tetraphenylborate, p-(t-octyl)benzenesulfonate, or the like.

The following are typical examples of the aromatic primary amine-type color developing agents having Formulas [IX], [X] and [X'], but the present invention is not limited thereto.

(1) o-aminophenol
(2) p-aminophenol
(3) 5-amino-2-oxytoluene
(4) 2-amino-3-oxytoluene
(5) 2-oxy-3-amino-1,4-dimethylbenzene
(6) N,N-diethyl-p-phenylenediamine hydrochloride
(7) N-methyl-p-phenylenediamine hydrochloride
(8) N,N-dimethyl-p-phenylenediamine hydrochloride
(9) N-ethyl-N-β-methanesulfonaminoethyl-3-methyl-4-aminoaniline and the sulfate thereof
(10) N-ethyl-N-β-hydroxyethylaminoaniline
(11) N,N-diethyl-3-(β-methanesulfonamidoethyl)-4-aminoaniline sulfate
(12) 4-amino-N-(2-methoxyethyl)-N-ethyl-3-methylaniline-p-toluenesulfonate
(13) N-ethyl-N-β-methanesulfonamidoethyl-3-methyl-4-aminoaniline tetraphenylborate
(14) 4-amino-N-(2-methoxyethyl)-N-ethyl-3-methylaniline tetraphenylborate
(15) p-morpholinoaniline
(16) p-piperidinoaniline
(17) 4-amino-N,N-diethyl-3-chloroaniline In the present invention, the previously mentioned color development can be carried out in usual manner, for example, the color development is made in a color developer bath containing the color developing agent of the present invention. Alternatively, the color developing agent of the invention or the precursor thereof is incorporated in advance in the silver halide photographic light-sensitive material used in the present invention, and this light-sensitive material is processed in an activator solution. After that it is bleached, fixed or bleach-fixed, washed and then stabilized in usual manner.

In the present invention, the particularly preferred dye formed by the reaction of the photographic coupler of the invention with the color developing agent of the invention is an azomethine dye among those formed by 3-anilino-5-pyrazolone-type magenta couplers having Formula [VI] and color developing agents, p-phenylenediamine derivatives having Formula [X'], the said azomethine dye having the formula:

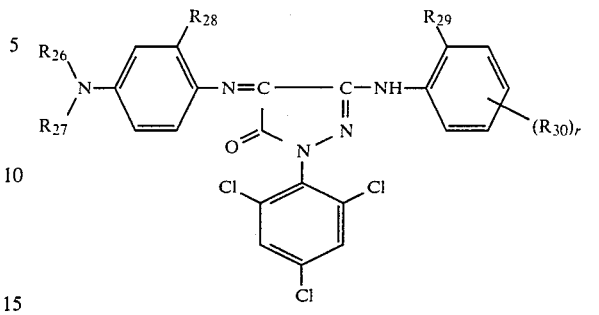

Formula [XI]

wherein $R_{26}$ and $R_{27}$ each is an alkyl radical (preferably an alkyl radical having from 1 to 4 carbon atoms), the alkyl radical represented by each of the $R_{26}$ and $R_{27}$ being allowed to having a substituent which includes alkylsulfonamido, alkoxycarbonyl, hydroxyl, and the like; $R_{28}$ is an alkyl radical (preferably an alkyl radical having from 1 to 4 carbon atoms); $R_{29}$ is a halogen (chlorine, bromine, fluorine or iodine), an alkyl radical (a straight-chain or branched-chain alkyl radical having from 1 to 4 carbon atoms, such as methyl, ethyl, i-propyl, t-butyl, etc.), or an alkoxy radical (a straight-chain or branched-chain alkoxy radical having from 1 to 4 carbon atoms, such as methoxy, ethoxy, t-butoxy, etc.); $R_{30}$ is a halogen (chlorine, bromine, fluorine or iodine) or a monovalent organic radical (preferably an alkylcarbonyl, alkylsulfamoyl, alkylamino or succinic acid imido radical, the succinic acid imido radical being allowed to have a substituent such as an alkyl, arylthio, or the like); and r is zero or 1.

EXAMPLES

The present invention is illustrated further in detail, but not limited by the examples below:

Example-1

Forty grams of Exemplified Magenta Coupler M-6 was dissolved into a mixture of 40 ml of Exemplified Organic Solvent H-3 and 100 ml of ethyl acetate. This solution was added to 300 ml of an aqueous 5% gelatin solution containing 25 g of sodium dodecylbenzenesulfonate. After that the mixture was dispersed by means of a homogenizer, and the dispersed liquid was mixed with 500 g of a green-sensitive silver halide chlorobromide emulsion (containing 30 g of Ag), and to this was then added a coating aid to thereby prepare a coating liquid. This coating liquid was coated on a polyethylene-coated paper support. On this coated layer was further coated another coating liquid containing 2-(2'-hydroxy-3',5'-di-t-amyl-benzotriazole), gelatin, coating aid and a hardener; the coating in this instance was made so that the coating quantities of the 2-(2'-hydroxy-3',5'-di-t-amyl-benzotriazole and the gelatin are 5 mg/dm$^2$ and 15 mg/dm$^2$, respectively, whereby a monochromatic silver halide photographic light-sensitive material was prepared. (This is called "blank sample" hereinafter.)

Next, Sample 1 was prepared in the same manner as in the blank sample except that Exemplified Metallic Complex (5) of this invention was added to the green-sensitive silver chlorobromide emulsion in a proportion of 0.2 mole per mole of the Magenta Coupler M-6.

Further, Sample 2 was prepared in the same manner as in the blank sample except that Comparative Metallic Complex A was added in a proportion of 0.2 mole per mole of the magenta coupler, the Comparative Metallic Complex A having the formula:

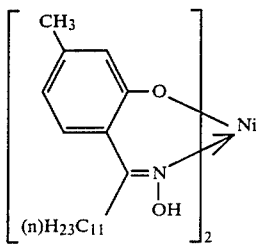

Further, Samples 3, 4 and 5 were prepared in the same manner as in Sample 1 escept that Exemplified High-Boiling Organic Solvents H-1 and H-8, and tricresyl phosphate as a comparative organic solvent, respectively, were added in place of the Organic Solvent H-3 used in Sample 1.

The thus prepared Samples 1 to 5 each was exposed through an optical wedge in a sensitometer (Model KS-7, manufactured by Konishiroku Photo Industry Co., Ltd.), and then processed in the following developing processes:

| Process | Temperature | Period |
| --- | --- | --- |
| Color developing | 32.8° C. | 3 minutes and 30 seconds |
| Bleach-fixing | 32.8° C. | 1 minute and 30 seconds |
| Washing | 32.8° C. | 3 minutes and 30 seconds |

The compositions of the processing liquids that were used in the above processes are as follows:

| Color Developer: | |
| --- | --- |
| 4-amino-3-methyl-N—ethyl-N—($\beta$-methane-sulfonamidoethyl)-aninline sulfate | 5 g |
| Benzyl alcohol | 15 ml |
| Sodium hexametaphosphate | 2.5 g |
| Anhydrous sodium sulfite | 1.85 g |
| Sodium bromide | 1.4 g |
| Potassium bromide | 0.5 g |
| Borax | 39.1 g |
| Water to make 1 liter. Use sodium hydroxide to adjust the pH to 10.3. | |

| Bleach-Fixer: | |
| --- | --- |
| Iron ammonium ethylenediamine-tetraacetate | 61.0 g |
| Diammonium ethylenediamine-tetraacetate | 5.0 g |
| Ammonium thiosulfate | 124.5 g |
| Sodium metabisulfite | 13.5 g |
| Anhydrous sodium sulfite | 2.7 g |
| Water to make 1 liter | |

In order to examine each of the samples with respect to the degree of being colored by the metallic complexes, measurements for the purpose were performed in the following procedures:

[Measurement of the colored degree]

The reflection spectrum of the white area of each sample was measured by means of a color analyzer Model 607 (manufactured by Hitachi, Ltd.), and the differences between the spectral reflection densities of the respective samples at 440 nm and that of the blank sample were found.

[Measurement of the increase in yellow stain]

Each sample was aged over a period of 14 days under an atmospheric condition of 77° C. with no humidification, and the increase in the blue-light density of each sample was measured by means of a densitometer, SAKURA Densitometer PDA-60.

The results are as given in Table 1.

TABLE 1

| Sample No. | Metallic complex | Organic Solvent | (Dielectric constant) | Colored density | Yellow stain |
| --- | --- | --- | --- | --- | --- |
| 1 (invention) | 5 | H-3 | (5.1) | 0.002 | 0.15 |
| 2 (comparative) | Comparative metallic complex A | H-3 | (5.1) | 0.016 | 0.15 |
| 3 (invention) | 5 | H-1 | (6.44) | 0.002 | 0.14 |
| 4 (invention) | 5 | H-8 | (4.5) | 0.002 | 0.14 |
| 5 (comparative) | 5 | Tricresyl phosphate | (6.9) | 0.002 | 0.37 |

As is apparent from Table 1, the samples of the invention show little or no color as compared to the conventional complex (Sample 2), and they are largely improved to prevent possible occurrence of yellow stain during their storage.

Example-2

The following layers were coated on a polyethylene-coated paper support in order from the support side to thereby prepare a multicolor silver halide photographic light-sensitive material.

First layer: Blue-sensitive silver halide emulsion layer comprised of an yellow coupler $\alpha$-pivaryl-$\alpha$-(1-benzyl-2,4-dioxoimidazolidine-3-yl)-2-chloro-5-[$\gamma$-(2,4-di-t-amylphenoxy)butylamido]-acetanilide (8 mg/dm$^2$), blue-sensitive silver halide emulsion (silver chlorobromide emulsion containing 90 mole% of silver bromide; silver equivalent of 3 mg/dm$^2$), 2,4-di-t-butylphenol-3',5'-di-t-amyl-4'-hydroxybenzoate (3 mg/dm$^2$), dioctyl phthalate (3 mg/dm$^2$) and gelatin (16 mg/dm$^2$).

Second layer: Interlayer comprised of 2,4-di-t-octylhydroquinone (1 mg/dm$^2$), diisodecyl phthalate (0.1 mg/dm$^2$) and gelatin (4 mg/dm$^2$).

Third layer: Green-sensitive silver halide emulsion layer comprised of Exemplified Magenta Coupler M-19 (4 mg/dm$^2$), green-sensitive silver chlorobromide emulsion (silver equivalent of (3 mg/dm$^2$), dioctyl phthalate H-3 (4 mg/dm$^2$) and gelatin (16 mg/dm$^2$).

Fourth layer: Interlayer comprised of ultraviolet absorbing agents 2-(2'-hydroxy-3',5'-di-t-amylphenol)- benzotriazole (3 mg/dm$^2$) and 2-(2'-hydroxy-3',5'-di-t-butylphenol)-benzotriazole (4 mg/dm$^2$), dioctyl phthalate (4 mg/dm$^2$) and gelatin (14 mg/dm$^2$).

Fifth layer: Red-sensitive silver halide emulsion layer comprised of a cyan coupler 2,4-dichloro-3-methyl-6-[-(2,4-di-t-amylphenoxy)butylamido]-phenol (4 mg/dm$^2$), dioctyl phthalate (2 mg/dm$^2$) and red-sensitive silver chlorobromide emulsion (silver equivalent of 3 mg/dm$^2$).

Sixth layer: Interlayer comprised of ultraviolet absorbing agents 2-(2'-hydroxy-3',5'-di-t-amylphenol)benzotriazole (2 mg/dm$^2$) and 2-(2'-hydroxy-3',5'-di-t-butylphenol)benzotriazole (2 mg/dm$^2$), dioctyl phthalate (2 mg/dm$^2$) and gelatin (6 mg/dm$^2$).

Seventh layer: Protective layer comprised of gelatin (9 mg/dm$^2$).

The thus prepared sample was regarded as Sample 6 (comparative).

Subsequently, Samples 7, 8, 9, 10 and 11 were prepared in the same manner as in Sample 6 except that 0.2 mole of each of Exemplified Metallic Complexes (5), (8), (10), (16) and (18) was added per mole of the magenta coupler to the third layer of Sample 6.

Further, Samples 12, 13, 14, 15 and 16 were prepared in the same manner as in Sample 8 except that Exemplified Organic Solvents H-1, H-8, H-14, and, as comparative solvents, diethyl phthalate and tricresyl phosphate were used in place of the Organic Solvent H-3 used in Sample 8.

Further, Sample 17 was prepared in the same manner as in Sample 8 except that in place of the metallic complex used in Sample 8 the following known antidiscoloration agent as Comparative Compound B was added in a quantity of 0.3 mole per mole of the coupler, the said Comparative Compound B having the formula:

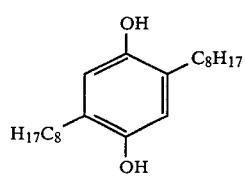

Still further, Samples 18 and 19 were prepared in the same manner as in Sample 8 except that Exemplified Magenta Couplers M-1 and M-23 were used in place of the Exemplified Coupler M-19 used in Sample 8.

The thus prepared samples 6 to 19 each was exposed in the same manner as in Example-1 (the exposure was made through an optical wedge to a green light in order to obtain magenta monochromatic color-developed samples.)

Each sample, after processing, was examined with respect to the colored degree and yellow stain produced thereon by way of the measurement made in the same manner as in Example 1.

Further, the resistances to light of these processed samples and of the same samples that were aged over a long period were measured in accordance with the following procedures:

[Light Resistance Test]

Each sample was placed in a device "Underglass Outdoor Exposure Stand" (manufactured by Suga Shikenki, K.K.) to expose the formed dye image to the direct sunlight over a period of 400 hours, and the discolored degree thereafter (Do-D/Do×100, wherein Do is the initial density (1.0), and D is discolored density) was measured.

[Aged Sample's Light Resistance Test]

Each dye-image-bearing sample was allowed to stand under an atmospheric condition of a temperature of 77° C. with no humidification over a period of 14 days, and after that the above light resistance test took place. The test results are as given in Table 2.

TABLE 2

| Sample No. | Magenta coupler | Metallic complex or compound | Organic solvent | Dielectric constant | Light resistance (discoloration %) | Aged light resistance (discoloration %) | Discolored density | Yellow stain |
|---|---|---|---|---|---|---|---|---|
| 6 (comparative) | M-19 | — | H-3 | 5.1 | 85 | 86 | 0.000 | 0.15 |
| 7 (invention) | " | 5 | " | " | 12 | 13 | 0.002 | 0.15 |
| 8 (invention) | " | 8 | " | " | 11 | 13 | 0.002 | 0.16 |
| 9 (invention) | " | 10 | " | " | 18 | 19 | 0.002 | 0.15 |
| 10 (invention) | " | 16 | " | " | 17 | 18 | 0.001 | 0.14 |
| 11 (invention) | " | 18 | " | " | 13 | 13 | 0.002 | 0.16 |
| 12 (nvention) | " | 8 | H-1 | 6.4 | 15 | 16 | 0.001 | 0.14 |
| 13 (invention) | " | " | H-8 | 4.6 | 11 | 12 | 0.002 | 0.15 |
| 14 (invention) | " | " | H-14 | 2.2 | 19 | 19 | 0.003 | 0.14 |
| 15 (comparative) | " | " | Diethyl phthalate | 7.6 | 29 | 35 | 0.002 | 0.37 |
| 16 (comparative) | " | " | Tricresyl phosphate | 6.9 | 30 | 39 | 0.002 | 0.40 |
| 17 (comparative) | " | Comparative compound B | H-3 | 5.1 | 55 | 57 | 0.000 | 0.15 |
| 18 (invention) | M-1 | 8 | " | " | 12 | 13 | 0.007 | 0.17 |
| 19 (invention) | M-19 | 8 | " | " | 10 | 11 | 0.002 | 0.16 |

As is apparent from Table 2, these samples of the invention show very small discoloration degrees despite the small adding mole quantities of the complexes as compared with Sample 17 containing the conventional oxidation inhibitor agent (Comparative Compound B). Also, the samples of the invention are less discolored and less yellow-stained (particularly in long-period aging). These effects can be accomplished only when the metallic complex of the invention and the organic solvent of the invention are combinedly applied to the magenta coupler of the invention, and these effects were all beyond expectation. In addition, satisfactory images which are immune to staining by as well as to adverse effects upon the emulsion's characteristics by the metallic complexes and stable against heat and light were obtained.

Example-3

Samples 20 and 21 were prepared in the same manner as in Samples 7 and 8, respectively, except that Exemplified Compound (7) as an antidiscoloration agent was used in a quantity of 20 mole% to the coupler in Samples 7 and 8. The Samples 6, 7, 8, 20 and 21 each was subjected to the same exposure as in Example 2, and then subjected to the same light resistance tests as in Example 2 to determine the degree of discoloration (%) of each sample. The test results are as given in Table 3.

TABLE 3

| Sample No. | Metallic complex | Antidiscoloration agent | Discoloration degree |
|---|---|---|---|
| 6 | — | — | 65 |
| 7 (invention) | Exemplified compound 5 | — | 11 |
| 8 (invention) | Exemplified compound 8 | — | — |
| 20 (invention) | Exemplified compound 5 | Exemplified compound (7) | 5 |
| 21 (invention) | Exemplified compound 8 | Exemplified compound (7) | 4 |

From Table 3 it is obvious that, although even Samples 7 and 8 that contain the metallic complex of the invention alone show a satisfactory antidiscoloration effect, Samples 20 and 21 that contain the metallic complex of the invention in combination with the antidiscoloration agent of the invention show a far more remarkable discoloration effect due to the sinergistic effect of these additives.

In addition, in the samples of the invention there occur no depositions of the metallic complex and antidiscoloration agent of the invention when preparing and coating their coupler-dispersed liquids, nor adverse effect upon the other photographic characteristics (fog, desensitization). Thus, the present invention enables to produce satisfactory color-developed images.

Example-4

In place of the Magenta Coupler M-19 that was used in Samples 6 and 7 of Example 2 the following Comparative Couplers a and b were used to prepare Samples 22, 23, 24 and 25. Each of these samples was subjected to the same exposure and light resistance tests as in Example 2. The test results are as shown in Table 4.

TABLE 4

| Sample No. | Magenta coupler | Metallic complex | Discoloration degree |
|---|---|---|---|
| 6 (Blank) | M-19 | — | 65 |
| 7 (invention) | " | Exemplified complex (5) | 12 |
| 22 (comparative) | Comparative coupler a | — | 75 |
| 23 (comparative) | Comparative coupler a | Exemplified complex (5) | 64 |
| 24 (comparative) | Comparative coupler b | — | 73 |
| 25 (comparative) | Comparative coupler b | Exemplified complex (5) | 55 |

Comparative Coupler a (the magenta coupler described in Japanese Patent O.P.I. Publication No. 133734/1981)

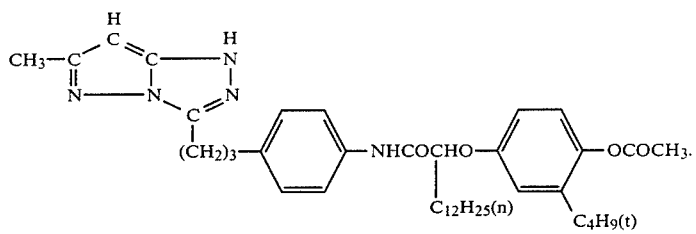

Comparative Coupler b

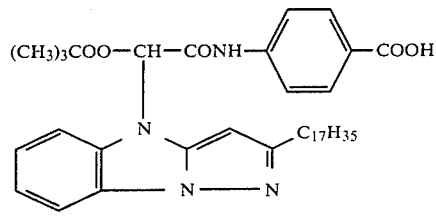

From Table 4 it is apparent that the metallic complex of the invention, when used in combination with, particularly, 3-amino-pyrazolone magenta coupler, shows a very high light resistance-improving effect.

What is claimed is:

1. A photographic element comprising a support having thereon a layer containing a silver halide emulsion and an anilino-type magenta coupler, wherein said layer comprises an organic solvent having a dielectric constant of not greater than 6.5 and a metallic complex having the following Formula (Ia), (IIa), or (IIIa):

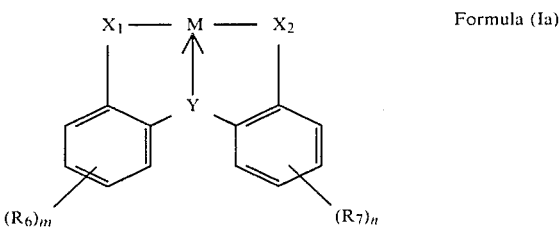

Formula (Ia)

-continued

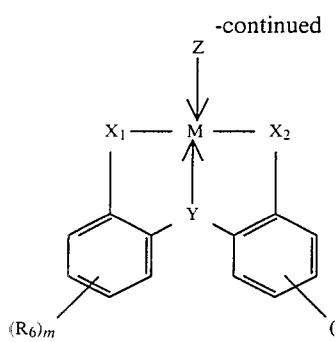
Formula (IIa)

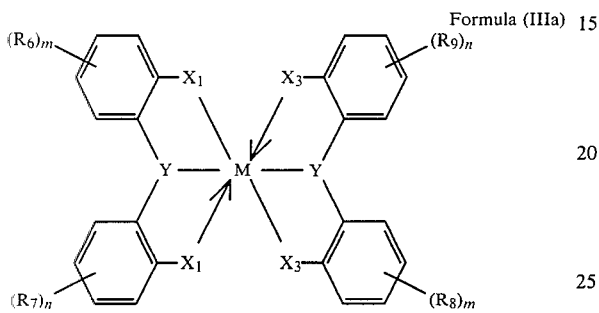
Formula (IIIa)

wherein M is nickel, copper, cobalt, palladium or platinum; $X_1$ and $X_2$ each is oxygen, sulfur or $-NR_5$, wherein $R_5$ is hydrogen or an alkyl, aryl or hydroxyl radical; $X_3$ is a hydroxyl or mercapto radical; Y is oxygen or sulfur; Z is a compound coordinatable to M; and $R_6$, $R_7$, $R_8$ and $R_9$ each is an alkyl radical, an aryl radical, an alkoxy radical, an aryloxy radical, an alkoxycarbonyl radical, an aryloxycarbonyl radical, an acylamino radical, an arylamino radical, an alkylamino radical, a carbamoyl radical, a sulfamoyl radical, a sulfonamide radical, a sulfonyl radical, or a cycloalkyl radical; m and n each is an integer of from zero to 4.

2. An element according to claim 1, wherein $X_1$ and $X_2$ of said metallic complex having said Formula [Ia], [IIa] or [IIIa] are oxygen atoms or sulfur atoms.

3. An element according to claim 1, wherein $X_1$ and $X_2$ of said metallic complex having said Formula [Ia], [IIa] or [IIIa] are oxygen atoms.

4. An element according to claim 1, wherein $X_3$ of said metallic complex having said Formula [IIIa] is a hydroxyl radical.

5. An element according to claim 1, wherein Y of said metallic complex having said Formula [Ia], [IIa] or [IIIa] is sulfur atom.

6. An element according to claim 1, wherein M of the metallic complex having said Formula [Ia], [IIa] or [IIIa] is one selected from the group of nickel, copper and cobalt.

7. An element according to claim 1, wherein M of the metallic complex having said Formula [Ia], [IIa] or [IIIa] is nickel.

8. An element according to claim 1, wherein Z of the metallic complex having said Formula [IIa] is a straight-chain or branched chain alkyl-containing alkylamine.

9. An element according to claim 8, wherein the alkyl radical of said alkylamine has 2 to 36 carbon atoms in total.

10. An element according to claim 8, wherein the alkyl radical of said alkylamine has 3 to 24 carbon atoms in total.

11. An element according to claim 1, wherein the metallic complex having the Formula [I], [II] or [III] has the following Formula [Ib], [IIb] or [IIIb];

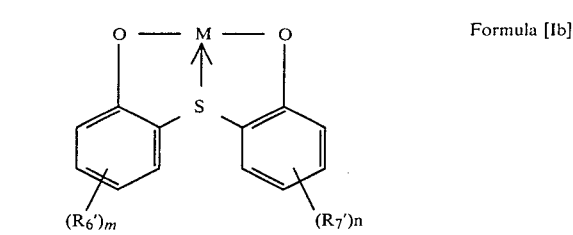
Formula [Ib]

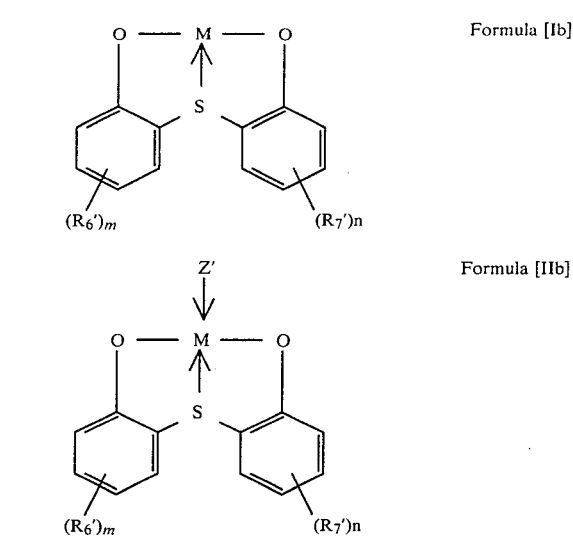
Formula [IIb]

Formula [IIIb]

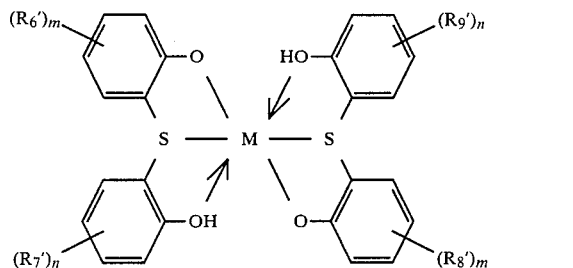

wherein M, m and n are defined synonymously with those in the Formula [Ia], [IIa] or [IIIa]; and, Z' is an alkylamine; and $R_6'$, $R_7'$, $R_8'$ and $R_9'$ each is a straight-chain or branched chain alkyl radical having not less than 4 carbon atoms.

12. An element according to claim 11, wherein $R_6'$, $R_7'$, $R_8'$ and $R_9'$ each is a straight-chain or branched chain alkyl radical having 8 to 22 carbon atoms.

13. An element according to claim 11, wherein the metallic complex has the Formula [IIb].

14. An element according to claim 1, wherein said organic solvent is the high-boiling organic solvent having a dielectric constant of 1.9 to 6.5.

15. An element according to claim 14, wherein said organic solvent is one selected from the group of phthalates and phosphates.

16. An element according to claim 15, wherein said phthalate is one having the following Formula [IV];

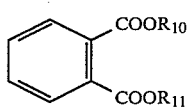
Formula [IV]

wherein $R_{10}$ and $R_{11}$ each is an alkyl, alkenyl or aryl radical, provided that the total number of the carbon atoms of the radicals represented by $R_{10}$ and $R_{11}$ is 8 to 32.

17. An element according to claim 16, wherein the total number of the carbon atoms of the radicals represented by $R_{10}$ and $R_{11}$ in the Formula [IV] expressing the phthalates is from 16 to 24.

18. An element according to claim 15, wherein said phosphates are those having the following Formula [IV];

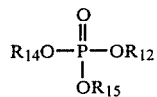

wherein $R_{12}$, $R_{13}$ and $R_{14}$ each is an alkyl, alkenyl or aryl radical, provided that the total number of the carbon atoms of the radicals represented by $R_{12}$, $R_{13}$ and $R_{14}$ is from 24 to 54.

19. An element according to claim 1, wherein said anilino-type magenta coupler is a 3-anilino-5-pyrazolone-type magenta coupler.

20. An element according to claim 1 wherein said anilino-type magenta coupler is a 3-anilino-5-pyrazolone-type magenta coupler having the following Formula [VI];

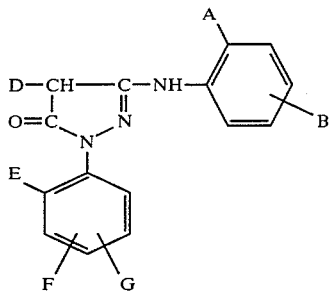

wherein A is a halogen, an alkyl radical, an aryl radical, an alkoxy radical, an aryloxy radical, a cyano radical, a nitro radical or a hydrogen atom; B is hydrogen, a halogen or a monovalent organic radical; D is hydrogen or a radical that can split off from the magenta coupler having Formula [IV] with the reaction on the oxidant of a color developing agent; E is a halogen, an alkyl, alkoxy, alkoxycarbonyl, nitro, aryloxy, cyano or acylamino radical; and, F and G are hydrogen or the same radical as those represented by E, respectively.

21. An element according to claim 1, wherein $R_1$, $R_2$, $R_3$ and $R_4$ represented by Formula [I], [II] and [III] each is a hydrogen atom or an alkyl radical.

22. An element according to claim 1 wherein said metallic complex is present in an amount of 5-100% by weight of the quantity of said coupler.

23. An element according to claim 22 wherein said metallic complex is present in an amount of 10-50% by weight of the quantity of said coupler.

24. A method of improving the light resistance of a dye image formed in a photographic element which comprises incorporation of a metallic complex compound having Formula (Ia) (IIa) or (IIIa) described below and an organic solvent having a dielectric constant of not greater than 6.5 into a layer of said photographic element comprising a silver halide emulsion and an anilino-type magenta coupler:

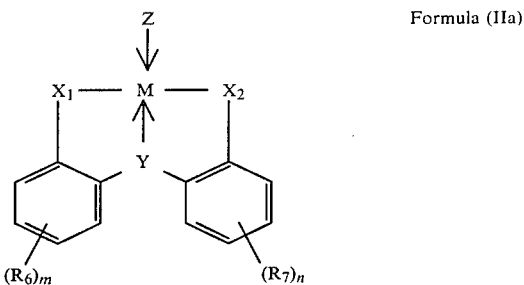

Formula (IIa)

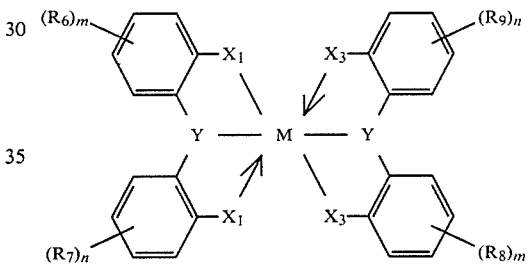

Formula (IIIa)

wherein M is nickel, copper, cobalt, palladium or platinum; $X_1$ and $X_2$ each is oxygen, sulfur or $-NR_5$, wherein $R_5$ is hydrogen or an alkyl, aryl or hydroxyl radical; $X_3$ is a hydroxyl or mercapto radical; Y is oxygen or sulfur; Z is a compound coordinatable to M; and $R_6$, $R_7$, $R_8$ and $R_9$ each is an alkyl radical, an aryl radical, an alkoxy radical, an aryloxy radical, an alkoxycarbonyl radical, an aryloxycarbonyl radical, an acylamino radical, an arylamino radical, an alkylamino radical, a carbamoyl radical, a sulfamoyl radical, a sulfonamide radical, a sulfonyl radical, or a cycloalkyl radical; m and n each is an integer of from zero to 4.

* * * * *